US009699866B2

(12) United States Patent
Jones

(10) Patent No.: US 9,699,866 B2
(45) Date of Patent: Jul. 4, 2017

(54) WAND GESTURE

(71) Applicant: MOJO LABS INC, Longmont, CO (US)

(72) Inventor: Morgan Jones, Longmont, CO (US)

(73) Assignee: MOJO LABS INC., Longmont, CO (US)

( * ) Notice: Subject to any disclaimer, the term of this patent is extended or adjusted under 35 U.S.C. 154(b) by 0 days.

(21) Appl. No.: 15/368,317

(22) Filed: Dec. 2, 2016

(65) Prior Publication Data

US 2017/0164448 A1 Jun. 8, 2017

Related U.S. Application Data

(60) Provisional application No. 62/261,861, filed on Dec. 2, 2015.

(51) Int. Cl.
*H03K 17/96* (2006.01)
*G06F 3/01* (2006.01)
*A61B 17/00* (2006.01)
*H05B 37/02* (2006.01)

(52) U.S. Cl.
CPC ..... *H05B 37/0227* (2013.01); *H05B 37/0272* (2013.01)

(58) Field of Classification Search
None
See application file for complete search history.

(56) References Cited

U.S. PATENT DOCUMENTS

2014/0225526 A1* 8/2014 Jonsson ................. H05B 37/02 315/291
2016/0205748 A1* 7/2016 Lashina ............. H05B 33/0851 315/130

* cited by examiner

*Primary Examiner* — Dedei K Hammond

(57) ABSTRACT

Some embodiments include a remote for gesture recognition for an external light system. In some embodiments, the remote may include an acceleration sensor; a wireless transceiver; memory; and a processor communicatively coupled with the acceleration sensor, the wireless transceiver, and the memory. In some embodiments, the processor may be configured to: sample acceleration data from the acceleration sensor; determine a first event type based on the acceleration data; determine a second event type based on the acceleration data; determine a command for an external system based on the first event type; and transmit the command to the external device using the wireless transceiver. In some embodiments, the first event type and/or the second event type comprises an event selected from the list consisting of a swipe, a tap, a double tap, a directional point, and a tilt; exclude the second event type.

27 Claims, 16 Drawing Sheets

WAND GESTURE

BACKGROUND

Gesture recognition may involve the use of facial recognition, voice recognition, lip movement recognition, eye tracking or other hand used gestures to interact with a machine or device. Gesture recognition has been currently used in various fields such as, the automotive sector, consumer electronics sector, transit sector, gaming sector, etc.

SUMMARY

Embodiments of the invention include a remote for gesture recognition in an external lighting system. The remote may include an acceleration sensor; a wireless transceiver; memory; and a processor communicatively coupled with the acceleration sensor, the wireless transceiver, and the memory. In some embodiments, the processor is configured to sample first acceleration data and second acceleration data from the acceleration sensor; determine a first event type based on the first acceleration data, wherein the first event type comprises one or more events selected from the list consisting of a swipe, a tap, a double tap, a directional point, and a tilt; determine a second event type based on the second acceleration data, wherein the second event type comprises one or more events selected from the list consisting of a swipe, a tap, a double tap, a directional point, and a tilt; exclude the second event type; determine a command for an external lighting system based on the first event type; and transmit the command to the external lighting system using the wireless transceiver.

In some embodiments, the acceleration data comprises a vector of accelerometer values along x-axis, y-axis, and z-axis.

In some embodiments, excluding the second event occurs when it is determined that the second event is similar to the first event but time lagged.

In some embodiments, the first event comprises an acceleration along a first axis and the second event comprises an acceleration along one or more axes orthogonal to the first axis.

In some embodiments, determining a first event type based on the acceleration data further comprises determining whether at least a portion of the acceleration data is greater than a first threshold value, and wherein determining a second event type based on the acceleration data further comprises determining whether the at least a portion of the acceleration data is greater than a second threshold value.

In some embodiments, the remote may include a touch sensor, and wherein the processor may be further configured to: receive grip data from the touch sensor indicating that a user has gripped the remote prior to transmitting the command to the external device; and determine whether the grip data is greater than a threshold, wherein the command is transmitted to the external device using the wireless transceiver in the event the grip data is greater than the threshold.

In some embodiments, the first event type comprises a tilt of the remote, and the command comprises a command to dim lights a given dim amount at the external lighting system.

In some embodiments, the given dim amount corresponds with the first acceleration data.

In some embodiments, the first event type comprises a swipe; and wherein the command for an external lighting system comprises a command to change the color an amount proportional to the swipe.

Some embodiments include a method comprising receiving an acceleration value generated by an acceleration sensor in response to a physical motion of a remote; comparing the acceleration value with a threshold value; determining an action to be taken at an external lighting system, based on the comparison; and sending a command to the external lighting system based on the action determined.

In some embodiments, the acceleration value corresponds with a tap, and the action to be taken comprises changing the state of the external lighting system.

In some embodiments, the acceleration value corresponds with a tilt, and the action to be taken comprises setting a dimming level of the external lighting system.

In some embodiments, the physical motion comprises gripping, tapping, conductor tapping, swiping, tilting, and/or pointing.

In some embodiments, the comparison is done on one axis in one direction and/or on multiple axes in multiple directions.

The remote may also perform a mathematical function on the acceleration value prior to comparing the acceleration value with a threshold value.

In some embodiments, the method may include receiving grip data from a touch sensor indicating that a user has gripped the remote prior to transmitting the command to the external device; and determining whether the grip data is greater than a threshold, wherein the command is transmitted to the external device using the wireless transceiver in the event the grip data is greater than the threshold.

In some embodiments, the method may include receiving grip data from a touch sensor indicating that a user has gripped the remote prior to transmitting the command to the external device; and entering a high power state.

Some embodiments include a remote for gesture recognition in an external lighting system. The remote may include a user interface sensor; a wireless transceiver; memory; and a processor communicatively coupled with the user interface sensor, the wireless transceiver, and the memory. In some embodiments, the processor may be configured to sample first sensor data and second sensor data from the user interface sensor; determine a first event type based on the first sensor data, wherein the first event type comprises one or more events selected from the list consisting of a swipe, a tap, a double tap, a directional point, a press and hold, a press, a hold, and a tilt; determine a second event type based on the second sensor data, wherein the second event type comprises one or more events selected from the list consisting of a swipe, a tap, a double tap, a directional point, a press and hold, a press, a hold, and a tilt; exclude the second event type; determine a command for an external lighting system based on the first event type; and transmit the command to the external lighting system using the wireless transceiver.

In some embodiments, the user interface sensor comprises either or both an accelerometer and a touch sensor.

In some embodiments, the remote may also include an accelerometer coupled with a processor. In some embodiments, the user interface sensor comprises a capacitive touch sensor. In some embodiments, the first event type comprises a combination of a tilt from the accelerometer and/or a hold on the user interface sensor. In some embodiments, the command for an external lighting system comprises a command to change the color an amount proportional to the swipe.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

DETAILED DESCRIPTION

In some embodiments, a remote for an improved user experience with lighting control is disclosed. In some embodiments, the user interface may interact with a lighting system using a remote that interprets gestures made by a person holding the remote and translates those gestures into commands for the lighting system. In some embodiments the remote may be an accelerometer-based remote.

In some embodiments, a remote may be used for advanced control of lighting. In other embodiments, a remote may be used for many other control systems, including control of sound, presentations, on/off state of appliances and many other possibilities.

Figure 1:
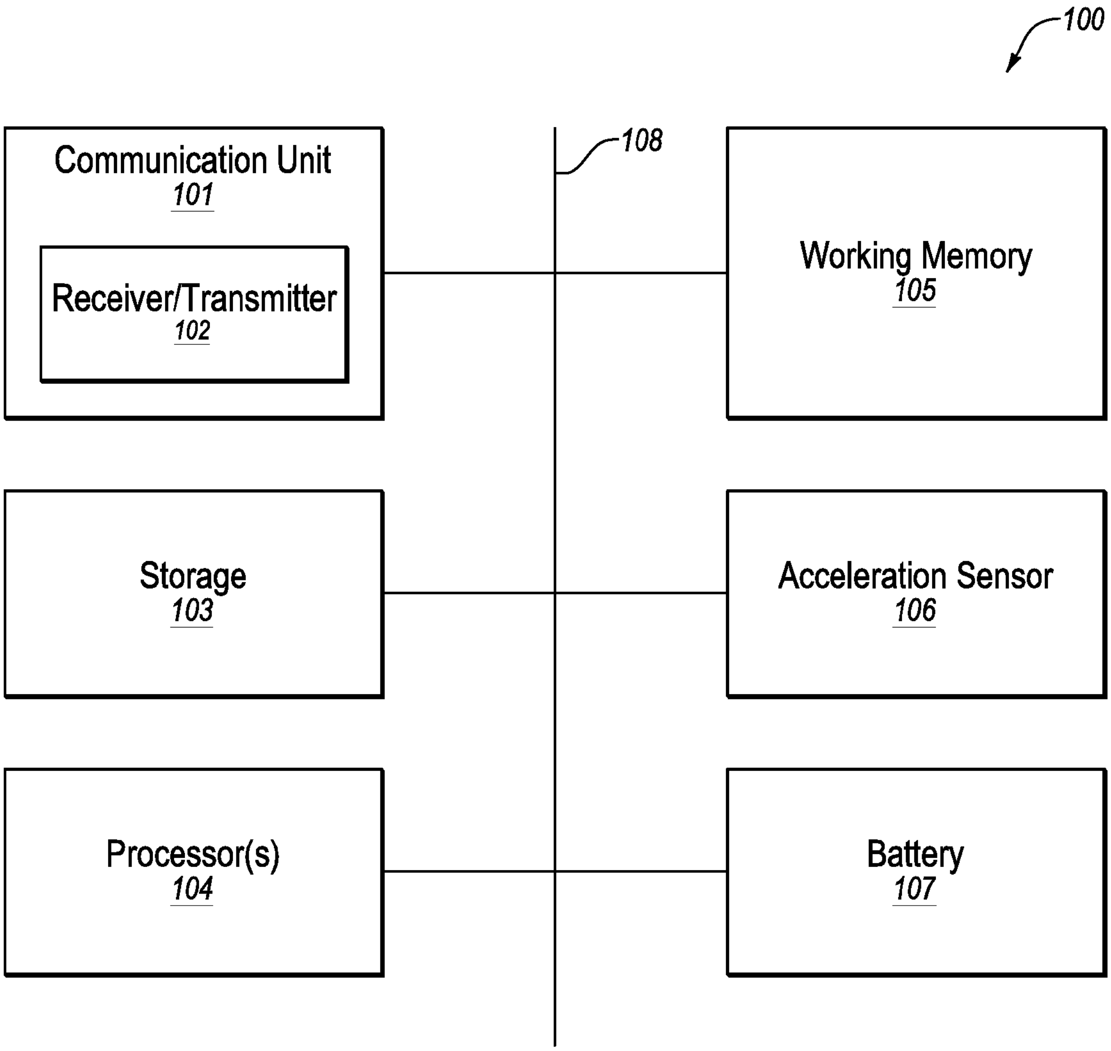
FIG. 1 is a block diagram of an example remote according to some embodiments of the invention.

FIG. 1 is a block diagram of an example remote 100 according to some embodiments. The remote 100 may include a communication unit 101, a storage device 103, processor(s) 104, a working memory 105, an acceleration sensor 106, and/or a battery 107. The communication unit 101, for example, may further include a transceiver 102.

In some embodiments, the remote 100 may include any or all of the hardware elements shown in the figure and described herein. The remote 100 may include hardware elements that can be electrically coupled via a bus 108 (or may otherwise be in communication, as appropriate). The hardware elements can include one or more processors 104, including, without limitation, one or more general-purpose processors and/or one or more special-purpose processors (such as digital signal processing chips, graphics acceleration chips, and/or the like).

In some embodiments, the remote 100 may include (and/or be in communication with) one or more storage devices 103, which can include, without limitation, local and/or network-accessible storage devices and/or can include, without limitation, an optical storage device, a solid-state storage device, such as random access memory ("RAM") and/or read-only memory ("ROM"), which can be programmable, flash-updateable, and/or the like. The remote 100 might also include a communications unit 101, which can include, without limitation, a modem, a network card (wireless or wired), an infrared communication device, a wireless communication device, and/or chipset (such as a Bluetooth® device, an 802.6 device, a WiFi device, a WiMAX device, cellular communication facilities, etc.), and/or the like. The communications unit 101 may permit data to be exchanged with a network, for example a lighting system, and/or any other devices described herein. In many embodiments, the remote 100 will further include a working memory 105, which can include a RAM or ROM device, as described above.

In some embodiments, the remote 100 also can include software elements, shown as being currently located within the working memory 105, including an operating system and/or other code, such as one or more application programs, which may include computer programs of the invention, and/or may be designed to implement methods of the invention and/or configure systems of the invention, as described herein. For example, one or more procedures described with respect to the method(s) discussed below might be implemented as code and/or instructions executable by a computer (and/or a processor within a computer). A set of these instructions and/or codes might be stored on a computer-readable storage medium, such as the storage device(s) 103 described above.

In some embodiments, the storage medium might be incorporated within the remote 100 or in communication with the remote 100. In other embodiments, the storage medium might be separate from the remote 100 (e.g., a removable medium, such as a flash drive, etc.), and/or provided in an installation package, such that the storage medium can be used to program a general-purpose computer with the instructions/code stored thereon. These instructions might take the form of executable code, which may be executable by the remote 100 and/or might take the form of source and/or installable code, which, upon compilation and/or installation on the remote 100 (e.g., using any of a variety of generally available compilers, installation programs, compression/decompression utilities, etc.), then takes the form of executable code.

Figure 2:
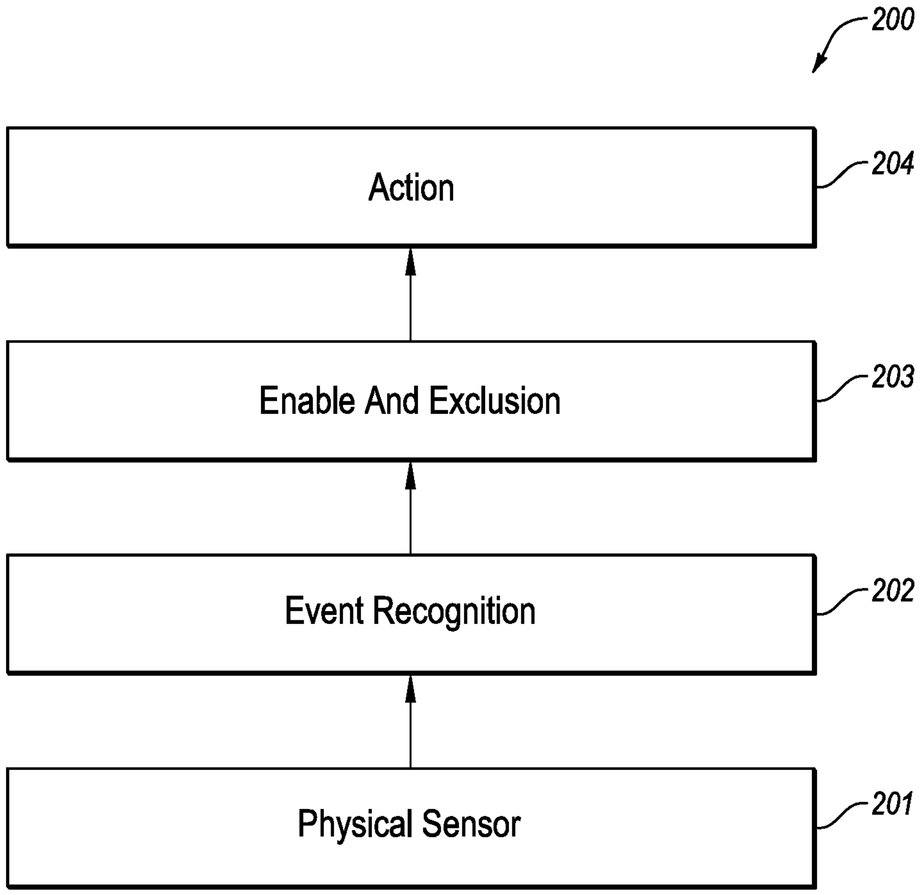
FIG. 2 is a block diagram of logical layers of the recognition problem according to some embodiments.

Some embodiments of the invention may include a layered approach to divide the recognition problem into logical layers, and then those layers may be combined in an innovative way to translate low level physical sensors into high-level events that ultimately control various things, for example, as seen in FIG. 2.

FIG. 2 shows an example of logical layers of the recognition problem according to some embodiments. Some embodiments may include four layers that may include: a physical sensor layer 201, an event recognition layer 202, an enable and exclusions layer 203, and/or an action layer 204. The event recognition layer 202, for example, may translate a raw input from the physical sensor layer 201 into time-tagged events, including: taps, swipes, points, and/or tilt information. The exclusions layer 203, for example, prevent information from moving up to the action layer 204. Finally the action layer 204 may take events and translate them into usable actions that ultimately affect control.

The physical sensor layer 201 may include, for example, receiving physical sensor data from accelerometers, buttons, sensors, touch screens, and/or other user interface elements. In some embodiments, the physical sensor data can be sampled at a sampling rate, time-tagged, and/or may be fed to the event recognition layer 202.

Any sampling rate and/or sampling precision can be used when sampling data from a sensor. In some embodiments, the sampling rate can be between 100-200 Hz. In other embodiments, the sampling rate can be 300-1000 Hz. In some embodiments, an accelerometer has a sampling rate of 200 Hz rate. In some embodiments, the accelerometer data may be signed 8 bit samples such as, for example, to be able to recognize short events such as taps. In some embodiments, the accelerometer data samples may be signed such as, for example, to be able to consider direction as a factor in detecting events. In other embodiments, the accelerometer may use 16-bit samples or 24-bit samples, for example, to achieve better resolution of the data being generated at the physical sensor layer 201. In some embodiments, the accelerometer data may be unsigned sample data.

In some embodiments, the event recognition layer 202 may receive physical sensor data from the physical sensor layer 201. In some embodiments, the physical sensor data received from the physical sensor layer 201 may be time tagged physical sensor data. The raw time-tagged physical sensor data may then be processed to detect various types of events such as, for example, tap, conductor tap, swipe, point, click, double tap, double swipe, and/or tilt. In some embodiments, this processing can partially occur in the acceleration sensor 106 within the physical sensor layer 201, some of which may comprise simple comparators and state machines to aid in detecting events including: tap, conductor tap, swipe, point and/or tilt.

In some embodiments, a tap may be defined as a shock event from the accelerometer's point of view, such that, for example, the remote 100 may be physically tapped to accomplish some action, wherein, a shock, for example, may include a sudden surge in acceleration. In some embodiments, the shock may include a sudden transient, such as for example an impulse response. In some embodiments, for lighting control, for example, the remote 100 may be tapped a first time to accomplish a light turn on action, and then subsequently can be tapped a second time to accomplish a light turn off action. This may offer a different and improved user experience over a simple button press.

In some embodiments, a tap can be detected by simply comparing an accelerometer value to a threshold as follows:

```
if (z > threshold)
    generate tap event
```

This comparison may be done on only one axis in one direction, or can also be performed on multiple axes in multiple directions. The action layer 204, for example, can select which types of levels, axes and/or directions it requests to be detected. In some embodiments, tap event detection may also optionally include or exclude the sign of the acceleration.

In some embodiments, tap event detection can also optionally be filtered to improve detection. A high pass filter, for example, may be used to remove the DC gravity vector detected by the accelerometer so that only changes to the overall vector are sent to tap detection. Various other filters maybe used.

In some embodiments, a "conductor tap" may be a slightly different tap where the person can be physically holding the remote 100 and then tapping the remote 100 on a surface. For example, the person may tap the remote 100 against a hard surface, such as a table. While a conductor tap might be recognized in the same way as a normal tap including an absolute value comparison, in some embodiments, an improved recognition of this event may include watching a tilt data from the accelerometer to see the swing of the remote 100 before and after the conductor tap.

In some embodiments, a swipe event may be an event generated when a person takes the remote 100 and swipes the remote 100 through the air in a direction and returns it to the neutral position. A swipe event may be a left swipe or a right swipe, which can map to actions that may affect a next and back action. Similarly, in some embodiments, a swipe up and a swipe down motion can map to increase or decrease actions at the application level.

In some embodiments, swipe events may be detected with a simple comparison of the acceleration level to a threshold, either in absolute value or in signed may be done. In some embodiments, the swipe event and the tap event need not be detected simultaneously. For example a horizontal swipe to the left may be detected with:

```
if (x < -threshold)
    generate swipe event
```

Figure 3:
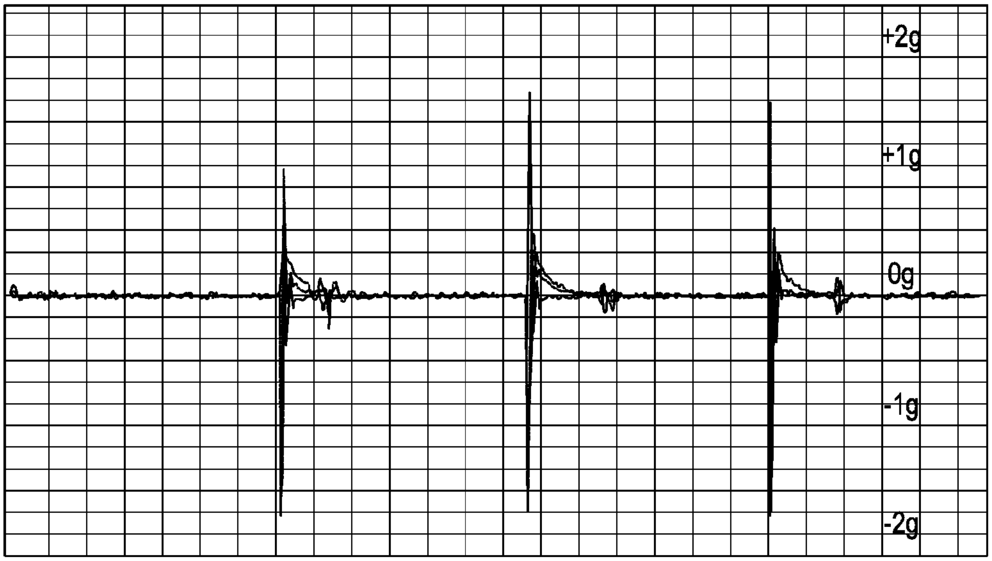
FIG. 3 shows example tap events at 200 Hz sample rate according to some embodiments.
Figure 4:
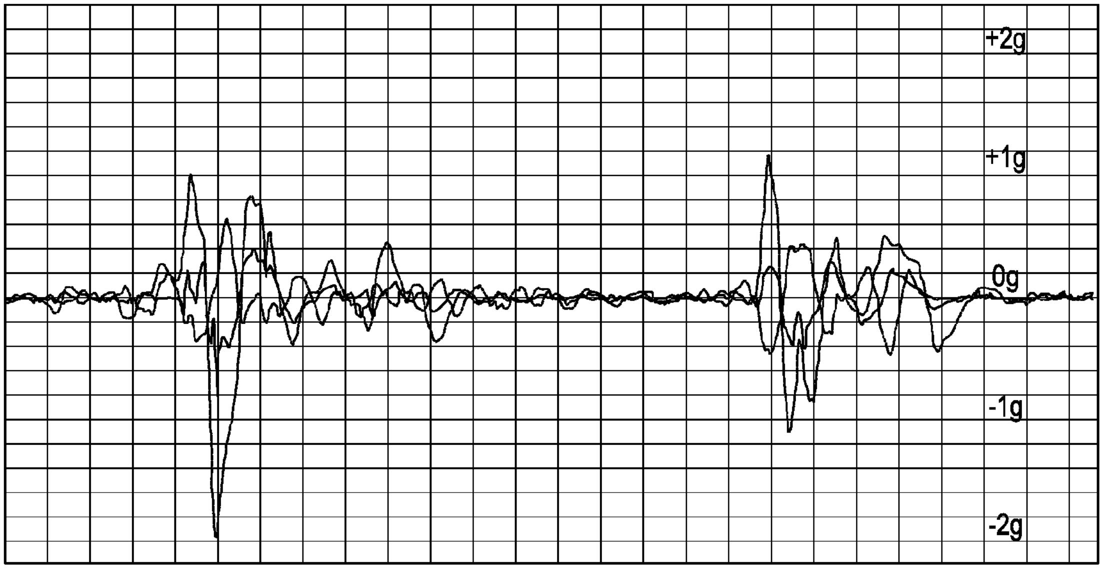
FIG. 4 shows example swipe events at 200 Hz sample rate according to some embodiments.

However, in some embodiments, where simultaneous detection may be required, the time duration of the swipe events can be taken into account. Whereas a tap event may be a very short shock event that may happen on a fast timescale, a swipe event may take place over a time scale that is longer, perhaps as much as 10-100 times as long. This time information can be combined with the level information to individually detect swipe events vs. tap events. For example FIG. 3 shows example tap events at 200 Hz sample rate and for example, FIG. 4 shows example swipe events at 200 Hz sample rate.

In some embodiments, point events may be used to initiate an action. For example, if the remote 100 is pointed at the ceiling, the pointing could begin an action such as the enabling of changing the dimming level of a light. Point events can be instantaneous, or may have a time requirement associated with them. For example, the remote 100 may be pointed in a direction for a certain amount of time for the event to be recognized.

Figure 5:
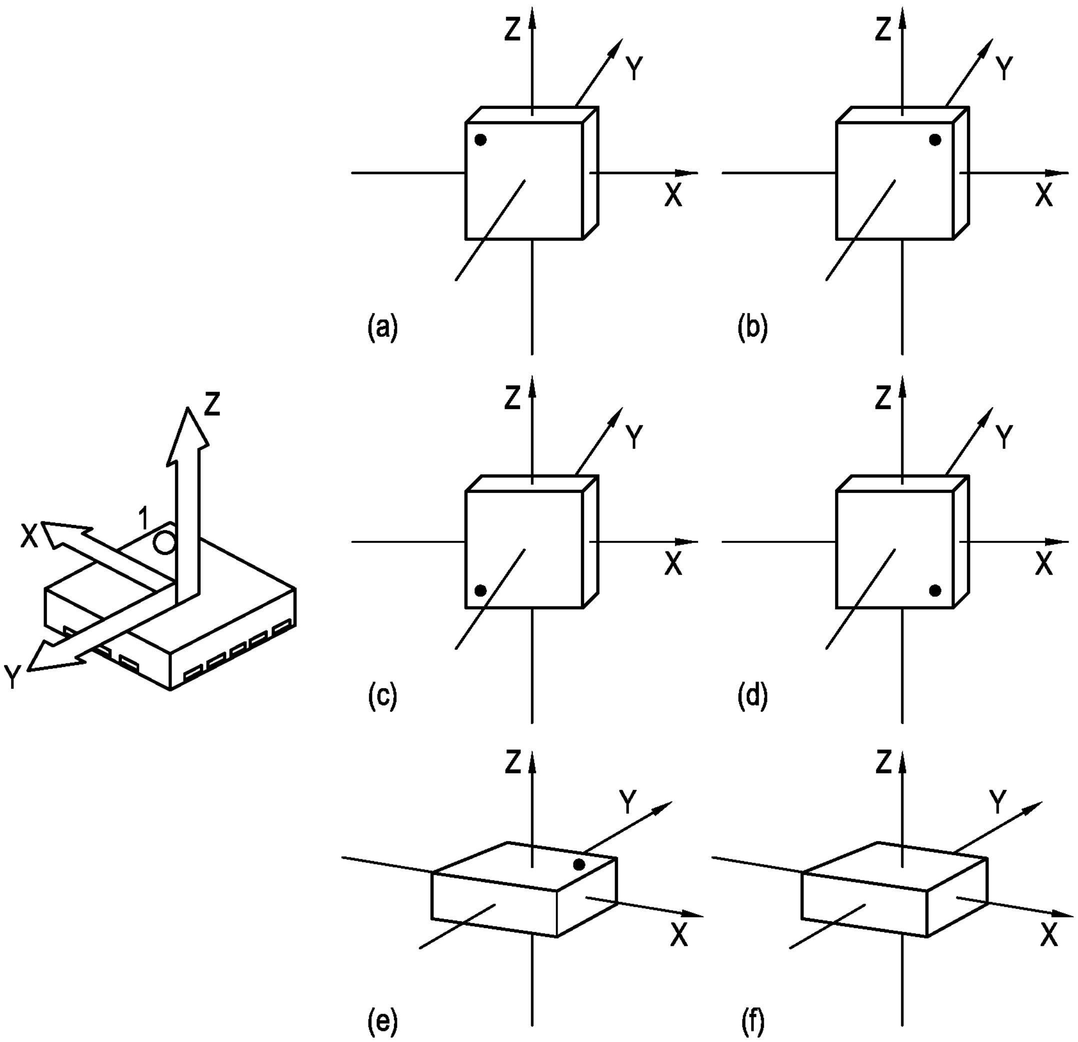
FIG. 5 is an example acceleration sensor according to some embodiments.

In some embodiments, any direction point can be recognized, the six axes may provide useful and meaningful directions for people using the remote 100: Up, Down, Roll Right, Roll Left, Nose up, Nose Down, for example, as can be seen in FIG. 5. In some embodiments, the point detection can also be thought of as an orientation detection.

In some embodiments, point detection can be accomplished by taking the raw accelerometer data and comparing

[x,y,z] vector to the vector of each of the six axes. In some embodiments, some pre-set values may be used to compare with the vector of the six axes. In the scenario where the vector difference is within a threshold, a point event may be enabled. For example for z axis point detection:

```
xa = Math.abs(x)
ya = Math.abs(y)
za = Math.abs(z)
 if ((xa < .zeroT) && (ya < .zeroT) && (za > .gravityT))
      if (z > 0)
            generate event POINT_Z_PLUS
     else
          generate event POINT_Z_MINUS
```

where, xa is the absolute value of x, ya is the absolute value of y and za is the absolute value of z, zeroT may be a value close to zero, and gravityT is a gravity vector, such that the x-axis point detection and the y-axis point detection may be determined in a similar manner. In some embodiments, for example, to determine a point in the Z-Plus-axis, for example, the X-axis and Y-axis may be close to zero, and the Z-axis may exceed a threshold close to a gravity vector. In units of g's of acceleration, for example, X and Y may be less than 0.2 g's, and Z may be greater than 0.8 g's. In some embodiments, this may match a POINT_Z_PLUS event. In some embodiments, where a time threshold may also be desired, the point match may be checked to have occurred for a certain amount of time before the point event is generated. For example, the time threshold for a point event could be greater than 1s or 2s before the event is generated, i.e., a person would hold the remote 100 for 1s or 2s to generate the point.

In some embodiments, a tilt detection may be a superset of point detection where the [x,y,z] vector of the acceleration data itself may be used. Any high-pass filtering, for example, can be disabled such that the accelerometer may measure the gravity vector directly to determine what orientation the unit may currently be in.

In some embodiments, tilt events may be useful, for example, for varying a value of action control at the action layer 204. For example, varying a tilt value can translate into varying the level of a light.

In some embodiments, tilt events can be single axes, or multi-axes. In some embodiments, a single axis may be most useful, but multiple axes data can also be taken into account.

In some embodiments, improved tap discrimination techniques may be used. For example, in an event detection differentiating between a tap or conductors tap vs. putting the remote 100 back down on a table can be difficult. For example, both the taps and "put down" actions on the part of a person can produce accelerations in all directions on the accelerometer. As another example, acceleration may be produced along the downward direction, which is being referred to as the z-axis direction, for the purpose of this discussion. The remote 100 may be configured, for example, such that the remote 100 may be able to differentiate the tap from the put down action, since the tapping action may be configured to trigger an actual event, whereas the put down action of the remote 100 may not be configured to trigger any events or actions.

In some embodiments, taps and put down actions may differ in their acceleration signature, such that taps may produce significantly more shock than a put down action, as taps may be more extreme actions. Furthermore, because of the shock that a tap may generate, the accelerometer, for example, can detect wide variations in acceleration during the event. The put down action may, for example, be gentler and while it may generate some acceleration, the magnitude of the put down action may be less than the magnitude of the tap. The variation over time of the put down action, for example, may also be less than the variation over time of the tap. The simple threshold rule may be used for detecting taps and rejecting put down's:

```
if (z > threshold)
      generate tap event
```

If the threshold is chosen well, the simple threshold rule may detect taps and reject some put downs. However, in some embodiments, it may not be a completely reliable rule. Instead, a better rule may be used, wherein the threshold may be detected as described above, followed by detecting if that same threshold is passed in the next N samples as a way of rejecting some put down events, i.e., the put down events might typically have one large acceleration value and then they may settle quite quickly, whereas the tap may take longer to settle.

```
if (z0 > threshold)
      if (z1, z2 or z3 > threshold)
      generate tap
```

where z0 is the initial sample, and z1, z2 and z3 are subsequent samples in time.

In some embodiments, this rule may reject put downs well, but may also reject some of the desired taps as well. As a result, in other embodiments, a different approach may be used, for example, the threshold detection may be implemented as shown in the above algorithm, and may be followed by one of the subsequent samples requiring to also pass a lower threshold in the opposite direction.

```
if (z0 > threshold1)
      if (zn < -threshold2)
      generate tap
if (z0 < -threshold1)
        if (zn > threshold2)
           generate tap
```

In some embodiments, this algorithm may watch z acceleration values for some number of samples after the initial threshold comparison, and then may compare the z acceleration values to a different threshold in the opposite direction, as for example in FIG. 6A and FIG. 6B. In other embodiments, the algorithm may watch the z values for 30 samples at 200 Hz, and/or may use a 2nd threshold of 1/2.5 of the initial threshold, which, in some embodiments, experimental testing has shown to be a reliable value. In some embodiments, the acceleration value may be needed to first exceed a threshold in one direction, and then subsequently pass a second threshold in the opposite direction, which may result in the tap events being detected, and the put down events being excluded.

Figure 6:
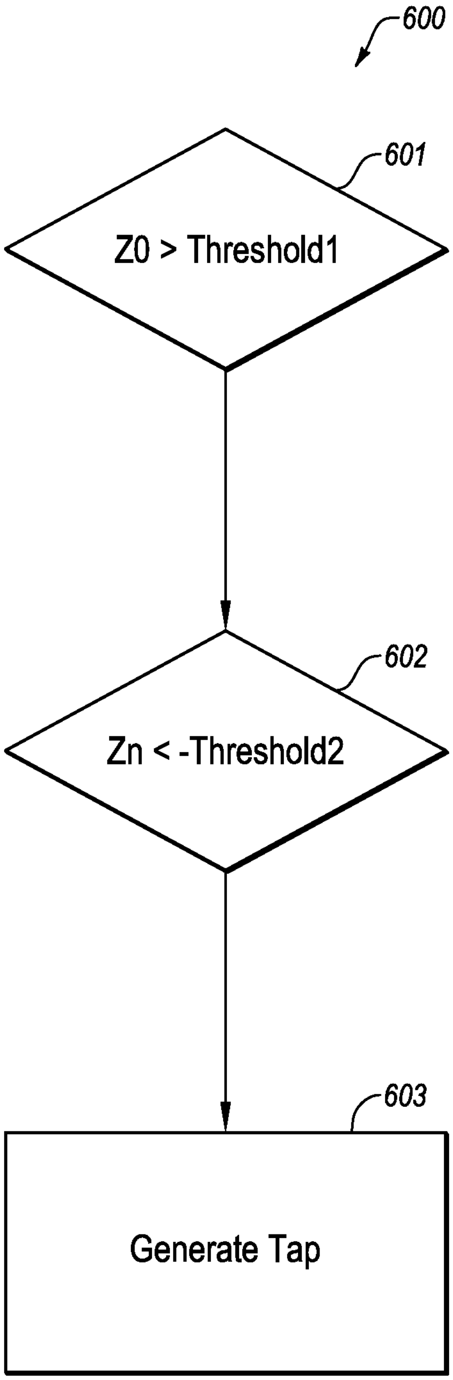
FIG. 6 is an example process of generating a tap according to some embodiments.

FIG. 6 is an example flowchart disclosing an example process 600 to detect a tapping motion, for example, at remote 100. At block 601, it may be determined whether the initial tap signal Z0 received from an acceleration sensor is greater than a first threshold (e.g., threshold1) in a first direction. At block 602, it may be determined whether a subsequent tap signal Zn is less than a second threshold (e.g., threshold2) in a direction opposite to the first direction.

In the event the initial tap signal Z0 is greater than a first threshold in the first direction, and the subsequent tap signal Zn is less than a second threshold in the direction opposite to the first direction, then a tapping event may be detected, as shown in block 603. In some embodiments, the absolute value of the tap signal may be used.

Returning to FIG. 2, the exclusions layer 203, for example, may help make a transition between the event recognition layer 202 and the actions layer 204 in the gesture recognition stack. The exclusions layer 203 may include different ways of looking at the same thing. For example, the exclusions layer 203, in some embodiments, may be configured for careful selection of what events may pass from the event recognition layer 202 to the higher action layer 204. In some embodiments, the exclusions layer 203 may for example, facilitate simple application action level processing with simple rules. In some embodiments, the exclusions layer 203 may also enable simpler detection algorithms in the event recognition layer 202.

In some embodiments, the simplest type of exclusion may be a single event exclusion. This may include event selection. For example, an exclusion may be set so that only taps on the Z-axis are forwarded to the action layer 204, and any signal along the X-axis and Y-axis are excluded. In some embodiments, this exclusion may be used for detecting taps when the remote 100 is set on a table, wherein the tap may happen in the Z direction, and so may exclude the motion along the X-axis and the Y-axis, if any. In some embodiments, this step may help zero in on the event desired.

In some embodiments, time exclusions may be more complicated, but may be critical in maintaining the simple functionality of the gesture recognition stack. In some embodiments, time exclusions may simply prevent an event from moving up the stack for a certain period of time such as, for example, when a Z-axis tap event happens, to prevent additional Z-axis taps for 500 ms, which may, for example, enable two benefits—the event recognition layer 202 may not need to worry about generating multiple Z-axis tap events for one physical tap because multiples can be masked by the exclusion. In some embodiments, the time exclusion may be set at 250 ms, 750 ms, 1,000 ms, 1,500 ms, etc. Additionally, it may enable very simple processing at the action layer 204 to turn the Z-axis tap into an on/off event. In some embodiments, a time exclusion may thus translate the very fast time scale of the accelerometer into the slower scale of human perception.

In some embodiments, time exclusion may be done, for example, by excluding point events for 5 seconds following the generation of a single point event. This can prevent inadvertent re-entry into an application-level adjustment mode when it is not desired.

In some embodiments, cross event exclusions may be the third type of exclusion. With this exclusion, one type of event may be excluded when another type of event is occurring, for example, excluding tap events when a point event is active.

In some embodiments, the action layer 204 may be responsible for receiving the events that are not excluded from the exclusions layer 203. In some embodiments, the action layer 204 may translate events into application-level actions. For example, the action layer 204 can translate a Z-axis tap into an action to turn on a light. In other embodiments, the action layer 204 may translate a tilt value measurement into a percent dimming command for a light.

In some embodiments, the action layer 204 may include some state information that is useful for taking some action. For example, to accomplish the turning on and off of a light in response to tap events, the action layer 204 may need to know whether the light is currently on or off, and so it may keep the state as on or off.

Figure 7:
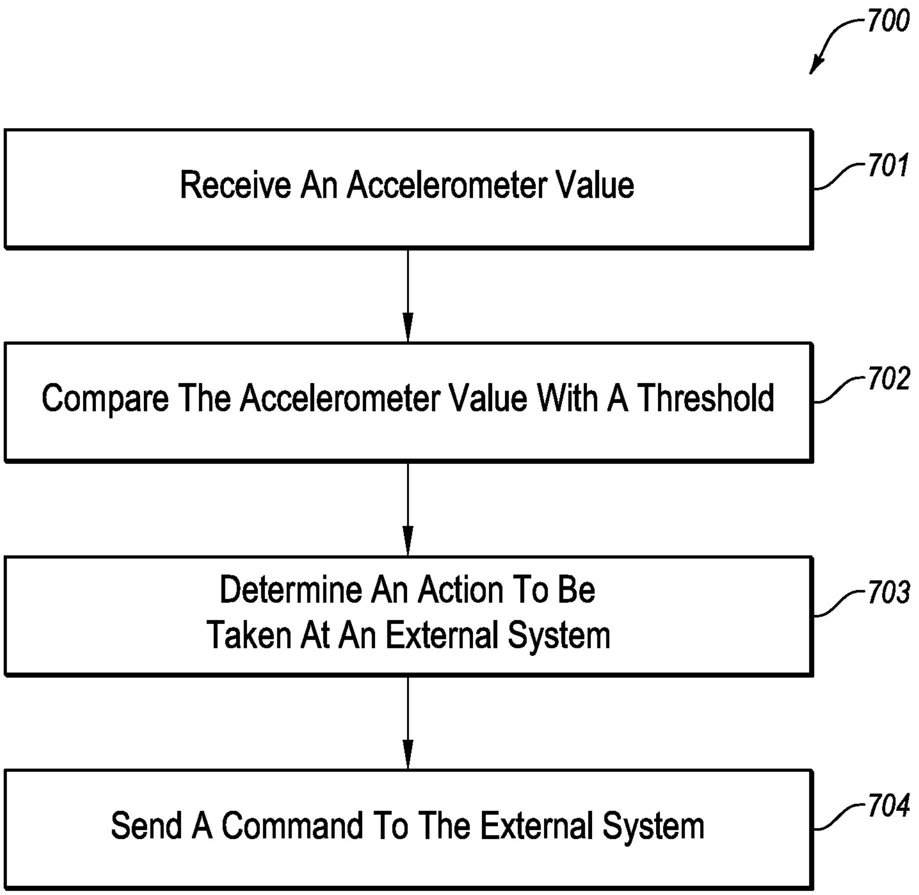
FIG. 7 shows a flowchart of an example process for using a remote to control an external system according to some embodiments.

FIG. 7 is an example flowchart showing the example process 700 of using a sensing device to control an external system. Although illustrated as discrete blocks, various blocks may be divided into additional blocks, combined into fewer blocks, or eliminated, depending on the desired implementation.

At block 701, the processor 104 of the remote 100 may receive an accelerometer value generated by the acceleration sensor 106 in response to a motion of the remote 100. For example, block 701 may include one or more of the actions described in the physical sensor layer 201. In some embodiments, the motion of the remote 100 may include gripping, tapping, conductor tapping, swiping, tilting and/or pointing, etc. In some embodiments, the accelerometer value may be sampled and time tagged. In some embodiments, the accelerometer value may either be an absolute value or a signed value. In some embodiments, the accelerometer data may include tilt data.

At block 702, the accelerometer value may be compared with a threshold value. In some embodiments, the threshold value may be preset within the processing system. In some embodiments, the comparison may be done on one axis in one direction and/or on multiple axes in multiple directions. For example, block 702 may include one or more of the actions described in the event recognition layer 202.

At block 703, an action to be taken at an external system may be determined based on the comparison between the accelerometer value and the threshold value. In some embodiments, for example, the action to be taken may include switching a light on or off, turning a volume up or down, changing light intensity levels, changing modes of operation of a device or system, etc. For example, block 703 may include one or more of the actions described in the event recognition layer 202 and/or the enable and exclusion layer 203.

At block 704, a command may be sent to the external system based on the action determined. In some embodiments, the external system may include a lighting system. In some embodiments, the external system may include an audio/video broadcasting system, etc. In some embodiments, the command upon reaching the external system may change the current settings of the external system based on the action determined.

In some embodiments, two consecutive tapping events can be configured to control a lighting system, by turning the light on and off: tap-tap (on-off). For example, as shown in FIG. 6, the action layer may translate tap events into turning on a light and then subsequently turning it off. In pseudo code, for example, this may translate to:

```
onTap:
    if ( state == lightOn)
            turn light off
          state = lightOff
          start time exclusion(500ms)
    else if (state == lightOff)
            turn light on
          state = lightOn
          start time exclusion(500ms)
```

In some embodiments, the tapping event may be preceded by receiving a starting signal. In some embodiments, the starting signal may include receiving an accelerometer value and/or a touch sensor value (e.g., from a touch sensor device such as, for example, a touch pad or a capacitive touch pad) when the user may grip the remote 100. In some embodiments, the processor 104 of the remote 100 may be woken from a low power mode and transitioned to a high power mode in the event the accelerometer value is greater than a threshold value. In the high power mode, the processor 104 of the remote 104 may analyze accelerometer data in the event the accelerometer value is greater than a threshold as notified by the Acceleration Sensor 106.

In some embodiments, in the event the accelerometer value is lesser than the threshold value, the processor 104 of the remote 100 may not be turned on. In some embodiments, the accelerometer value being lesser than the threshold value may indicate that the remote 100 may have been tapped on by a hand or rubbed against a hard surface, such as a table, etc., instead of being gripped or held by the user and the processor 104 may remain in a low power mode.

Figure 8:
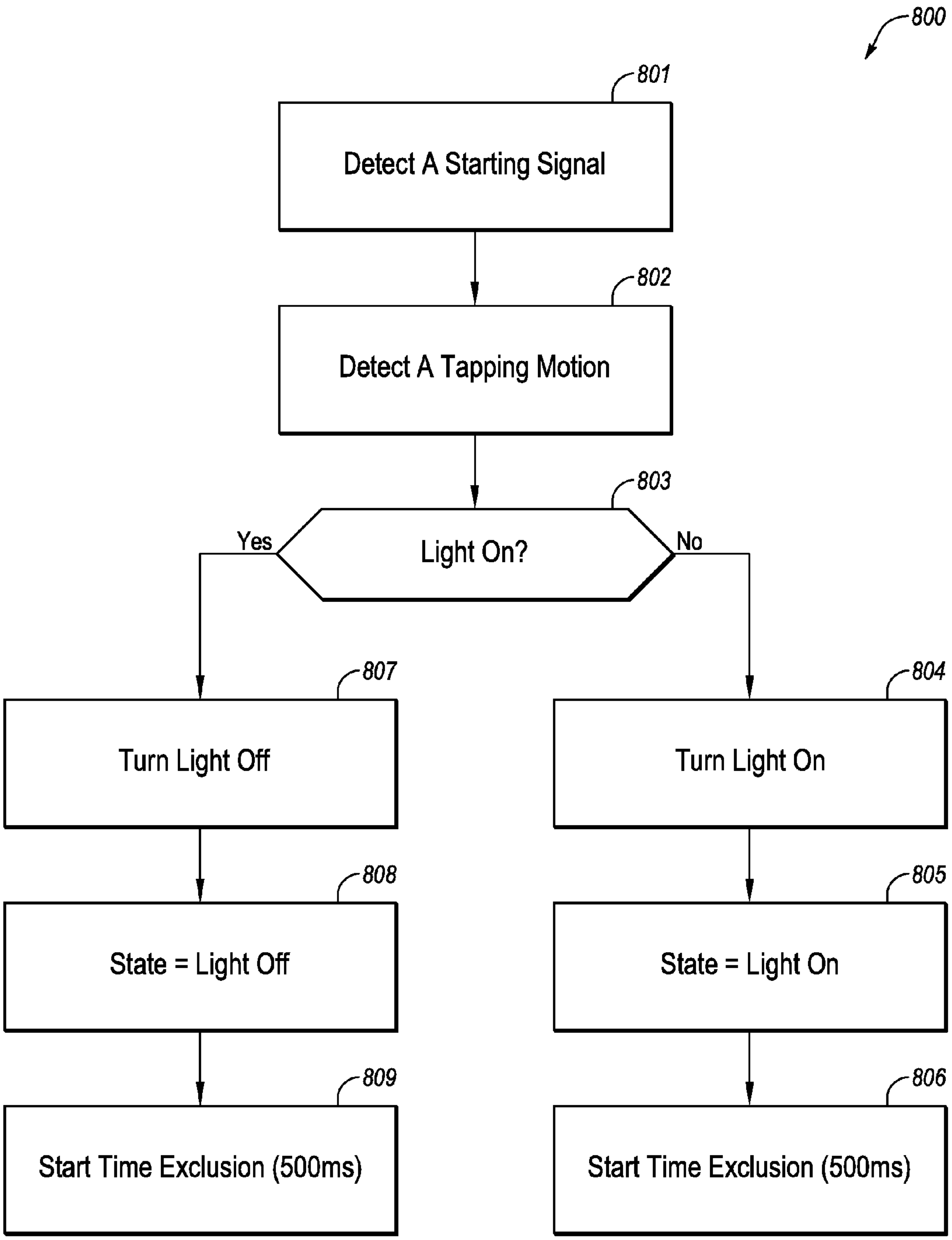
FIG. 8 is a flowchart of an example process for controlling an external device in response to a tapping event according to some embodiments.

FIG. 8 is a flowchart of an example process 800 of determining the working of the remote 100 in response to two tapping motions, according to some embodiments. Although illustrated as discrete blocks, various blocks may be divided into additional blocks, combined into fewer blocks, or eliminated, depending on the desired implementation.

At block 801, the remote 100 may detect a starting signal as a result of the remote 100 being gripped or held by a user. In some embodiments, the gripping of the remote 100 may be detected with a capacitive touch pad or other type of touch pad. In some embodiments, the starting signal may be generated in the event an acceleration value is received in response to the gripping of the remote 100 that is greater than a threshold. In some embodiments, the threshold may be preset.

At block 802, the remote 100 may detect a tapping motion. The tapping motion may be generated for example, by a user who may tap the remote 100 on a surface. The tapping motion may be detected, for example, when one or more accelerometer value exceeds a threshold value. In some embodiments, the tapping motion may be detected when a number of consecutive accelerometer values exceed the threshold. In other embodiments, the tapping motion may be detected when a number of consecutive accelerometer values exceed the threshold, followed by requiring one of the accelerometer values to pass a lower threshold in the opposite direction. For example, one of the accelerometer values may pass a lower threshold when the accelerometer value is lesser than a negative threshold value or when the accelerometer value is greater than a positive threshold value.

After detecting a tapping motion at the remote 100 at block 802, the remote 100 may transmit a signal to a lighting system at block 803. For example, this signal may request or detect the current status (or state) of one or more lights in the lighting system. For example, the remote 100 may check whether the light is 'On'. As another example, the remote 100 may check whether the light is 'Off'.

At block 804, after it may be detected that the light in the lighting system is 'Off', the light may be turned 'On' in response to the detected tap. For example, after the remote 100 may receive information from the lighting system that the light is 'On', the remote 100 may send a signal to the lighting system directing the light to be turned 'Off'. In some embodiments, the transmitting and receiving of signals between the remote 100 and the lighting system, may occur via the transceiver 102 present in the remote 100 and in a receiver unit of the lighting system.

At block 805, the current 'state' of the light may be saved as 'Off'. For example, the processor may assign to a variable 'state', the current state of the light, for example 'Off', and may save the variable into a memory of the remote 100.

At block 806, a time exclusion may be set such as, for example, at 500 ms, such that multiple tapping motion of the remote 100, may be excluded from causing the remote 100 to change the state of the light. The time exclusion may also be at 250 ms, 750 ms, 1,000 ms, 1,500 ms, etc. In some embodiments, for example, any tapping motion of the remote 100, after a single tapping motion may not be acted upon until the time exclusion period has been reached. For example, a processor within the remote 100, may detect the multiple tapping motion but may not send any signal or information to the lighting system to turn the light 'Off', based on any tapping motion that may occur during the time exclusion period after the first tapping motion.

Returning to block 803, if the light is in the 'Off' state then process 800 proceeds to block 807. At block 807, the light may be turned 'On'. For example, after the remote 100 may receive information from the lighting system that the light is 'Off' (or not in the 'On' state), the remote 100 may send a signal to the lighting system indicating that the light is to be turned 'On'. In some embodiments, the transmitting and receiving of signals between the remote 100 and the lighting system, may occur via a transceiver 102 present in the remote 100 and in a receiver unit of the lighting system.

At block 808 the current 'state' of the light may be saved as 'On'. For example, the processor may assign to a variable 'state', the current state of the light, for example 'On', and may save the variable into a memory of the remote 100.

At block 809 a time exclusion may be set at, for example 500 ms, such that multiple tapping motion of the remote 100, may be excluded. The time exclusion may also be at 250 ms, 750 ms, 1,000 ms, 1,500 ms, etc. In some embodiments, for example, any tapping motion of the remote 100, after a single tapping motion may not be acted upon until the time exclusion period has been reached. For example, a processor within the remote 100, may detect the multiple tapping motions but may not send any signal or information to the lighting system to turn the light 'On', based on any tapping motion that may occur for 500 ms after the first tapping motion.

Figure 9:
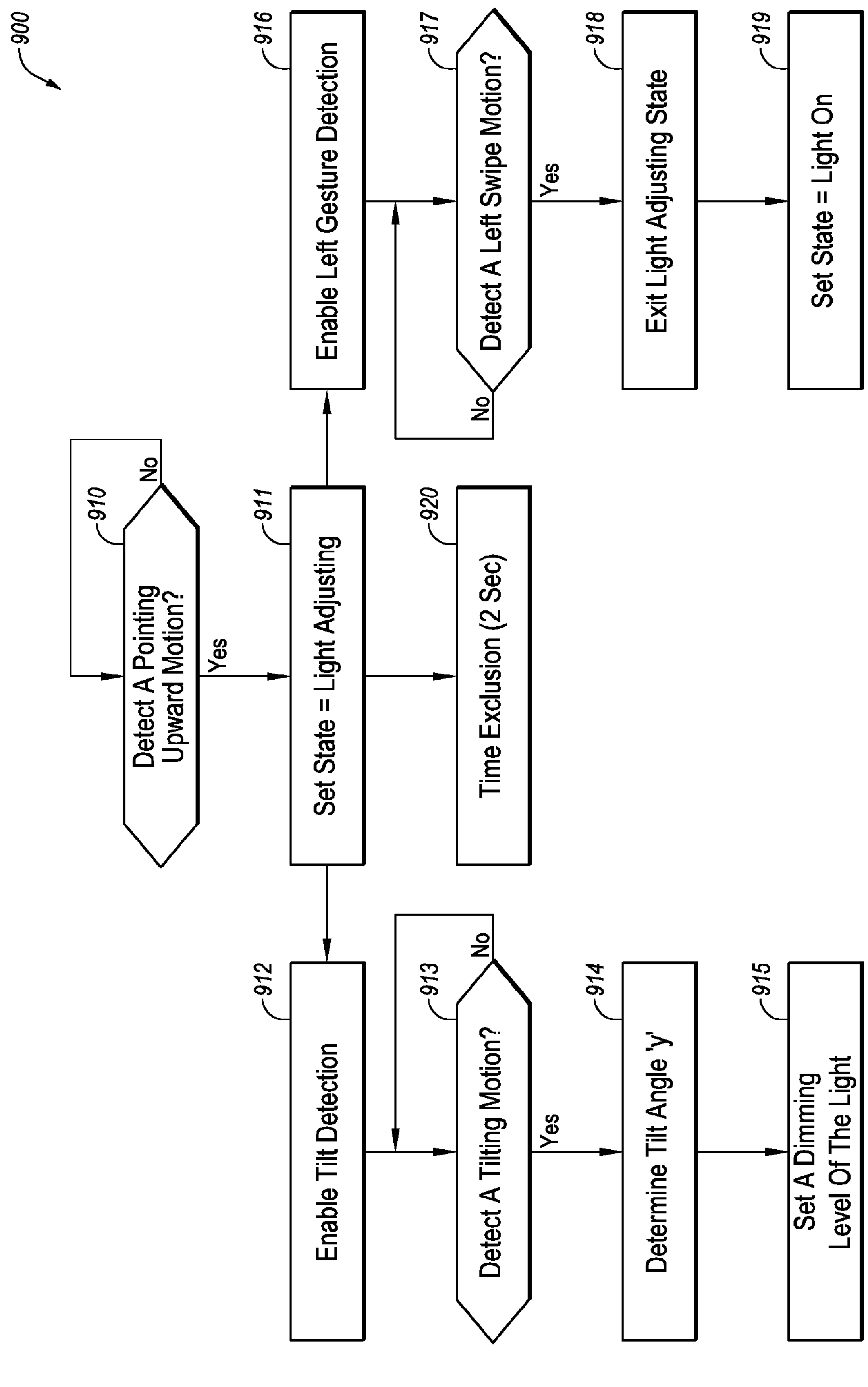
FIG. 9 is a flowchart of an example process for controlling an external device in response to pointing up and tilting motion according to some embodiments.

In some embodiments, after block 806 in FIG. 8, process 800 may end. In some embodiments, after block 806, process 800 may proceed to block 910 of process 900, as shown in FIG. 9. Although illustrated as discrete blocks, various blocks may be divided into additional blocks, combined into fewer blocks, or eliminated, depending on the desired implementation.

In some embodiments, in process 800 shown in FIG. 8 the light may first be turned on with a tap, followed by a point up event, which may then enter a light adjusting state where a tilt value of the remote 100 may directly set a dimming level of the light of the lighting system. This light adjusting state may then be exited, for example with a left swipe followed by a subsequent tap that may turn the light off. For example:

```
onTap:
if ( state == lightOn)
        turn light off
        state = lightOff
        start time exclusion(500ms)
else if (state == lightOff)
        turn light on
```

-continued

```
        state = lightOn
        start time exclusion(500ms)
          enable point up detect
onPointUp:
        state = lightAdjusting
        enable tilt
        enable left gesture detection
      set time exclusion for pointUp(2 seconds)
onTilt:
        set light level with tilt.y
onLeftGesture:
        state = lightOn
```

FIG. 9 is a flowchart of an example process for controlling an external device in response to pointing up and tilting motion according to some embodiments. Although illustrated as discrete blocks, various blocks may be divided into additional blocks, combined into fewer blocks, or eliminated, depending on the desired implementation.

At block 910, the remote 100 may be enabled to detect any pointing upward motion of the remote 100. For example, a pointing upward motion in the air may be done, using the remote 100, by the user. For example, a pointing up motion may be detected when the difference between an [x,y,z] vector of accelerometer values and a vector of preset values of six axes is within a threshold value. For example, the point up motion may be detected when the absolute value of the accelerometer value along the z-axis is greater than a first threshold and the absolute values of the accelerometer values along the x-axis and y-axis are lesser than a second threshold, and the accelerometer value along the z-axis is greater than zero. In some embodiments, the six axes may include up, down, right, left, nose up, and nose down.

At block 911, on detecting a pointing up motion of the remote 100, a light adjusting state may be activated. For example, once the remote 100 is pointed upwards, the processor may enable a feature of the remote 100 such that the remote 100 may be used to adjust the light level, and the variable 'state' is now set at 'lightAdjusting'. In some embodiments, on detecting a pointing up motion, the remote 100 may be configured to detect other different kinds of motion, such as for example, tilt motion and left gesture motion that may be used, for example, to adjust the light level.

At block 912, in the scenario where the light adjusting state is activated, the remote 100 may be configured to detect a tilt motion. For example, a tilt motion may be detected if the [x,y,z] vectors of the acceleration data is greater than a threshold value. In some embodiments, the tilt motion is used to vary the dimming level or the intensity of the light, in a lighting system.

At block 913, a motioning of the remote 100 may be checked for a tilting motion. In the event a tilting motion is detected, a tilt angle 'y' may then be determined at block 914. In some embodiments, upon the tilt motion being detected, for example, once the remote 100 is tilted, the processor may enable a feature of the remote 100 such that a variable 'light level' may be set at a tilt value, for example 'y'.

At block 915, a dimming level of the light of the lighting system may be adjusted which may be based on the tilt angle 'y'. In some embodiments, the more the tilt the more the light may be dimmed.

At block 916, in the scenario the light adjusting state is activated, the remote 100 may be configured to detect a left swiping motion or a left gesture.

At block 917, a motioning of the remote 100 may be checked for a left swiping motion. In the event a left swiping motion is detected, in some embodiments, the remote 100 may be configured to exit the light adjusting state, for example, as shown in block 918, and also may set the state of the light as 'On', for example as shown in block 919. In some embodiments, on detecting the left swiping motion of the remote 100, the processor may reset the variable 'state' to 'lightOn', indicating the current state of the light at the lighting system to be 'On' and also may deactivate the light adjusting state of the remote 100.

At block 912, a time exclusion may be set at, for example 2 seconds, such that multiple point up motions of the remote 100, may be excluded. In some embodiments, the time exclusion may be set at 0.5 second, 1 second, 5 seconds, 10 seconds, etc. In some embodiments, any pointing up motion of the remote 100, such as, for example, a single pointing up motion, may not be acted upon until the time exclusion period has been reached.

In some embodiments, a tapping motion of the remote 100, following the deactivation of the light adjusting state of the remote 100, may be detected as described in block 802 of process 800 and the light may be turned 'Off'.

Figure 10A:
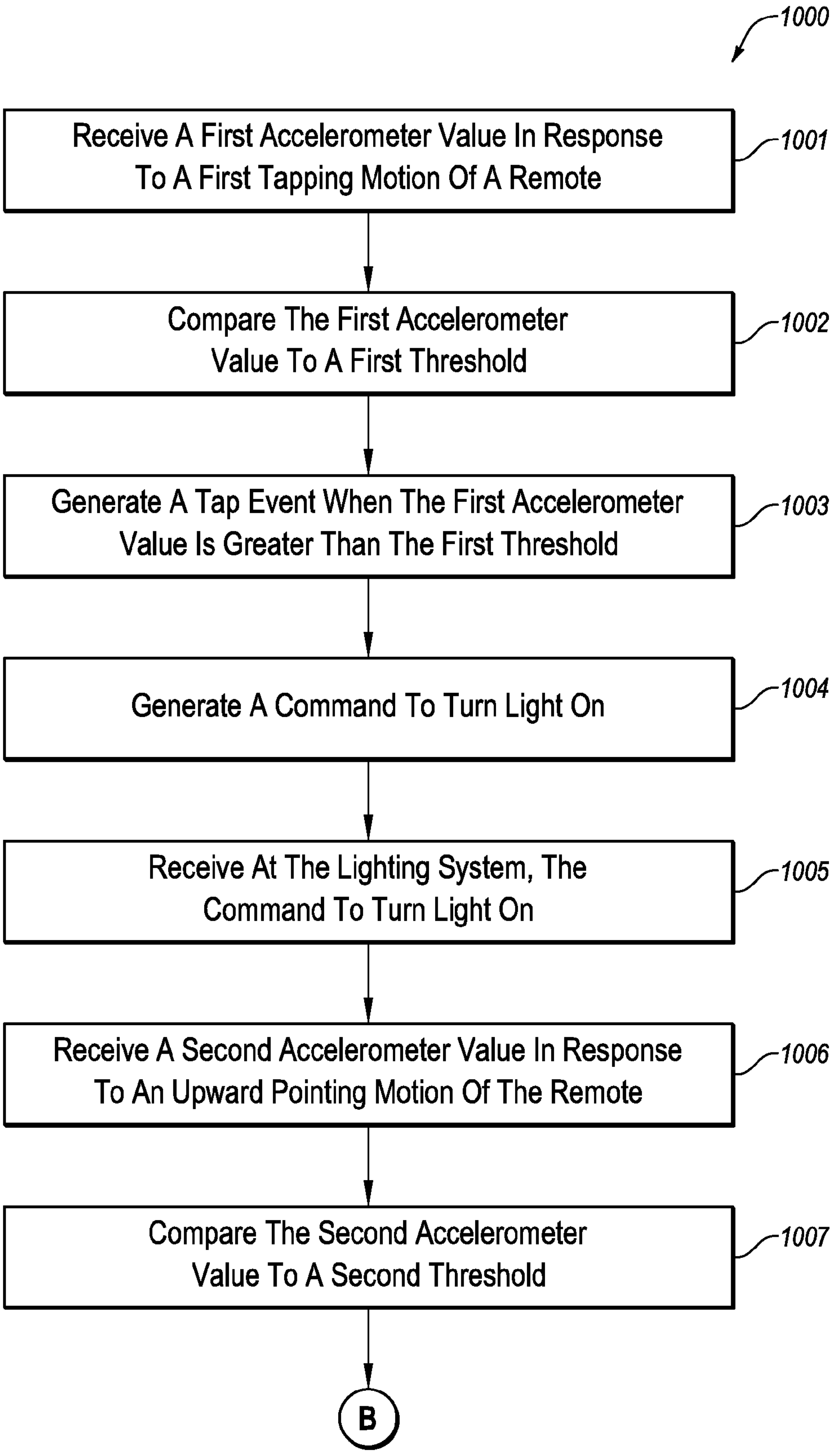
FIGS. 10A, 10B, and 10C are a flowchart of an example process for controlling an external device in response to tapping motion, pointing upward motion, tilting motion, and a left swiping motion according to some embodiments.
Figure 10B:
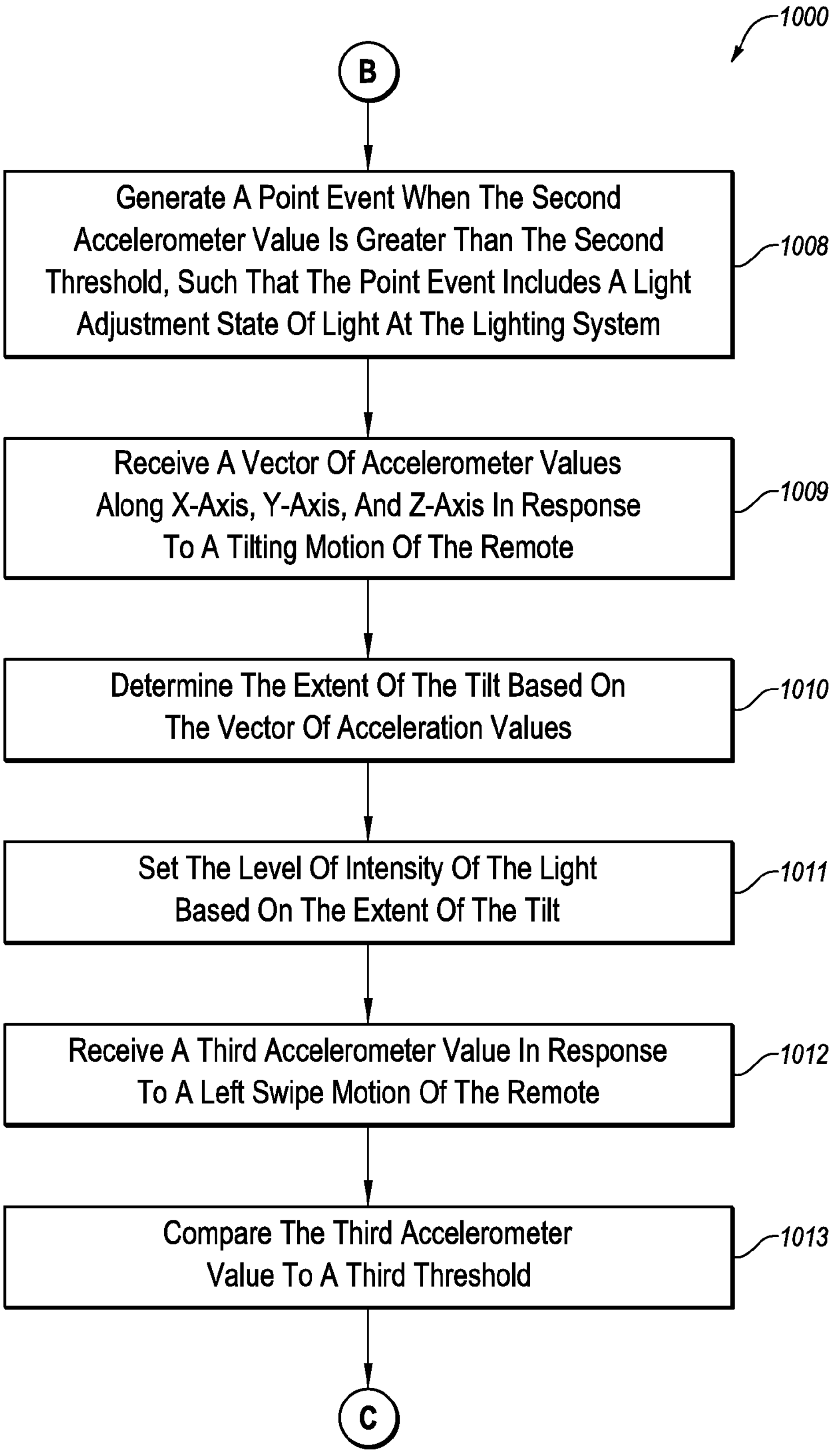
Figure 10C:
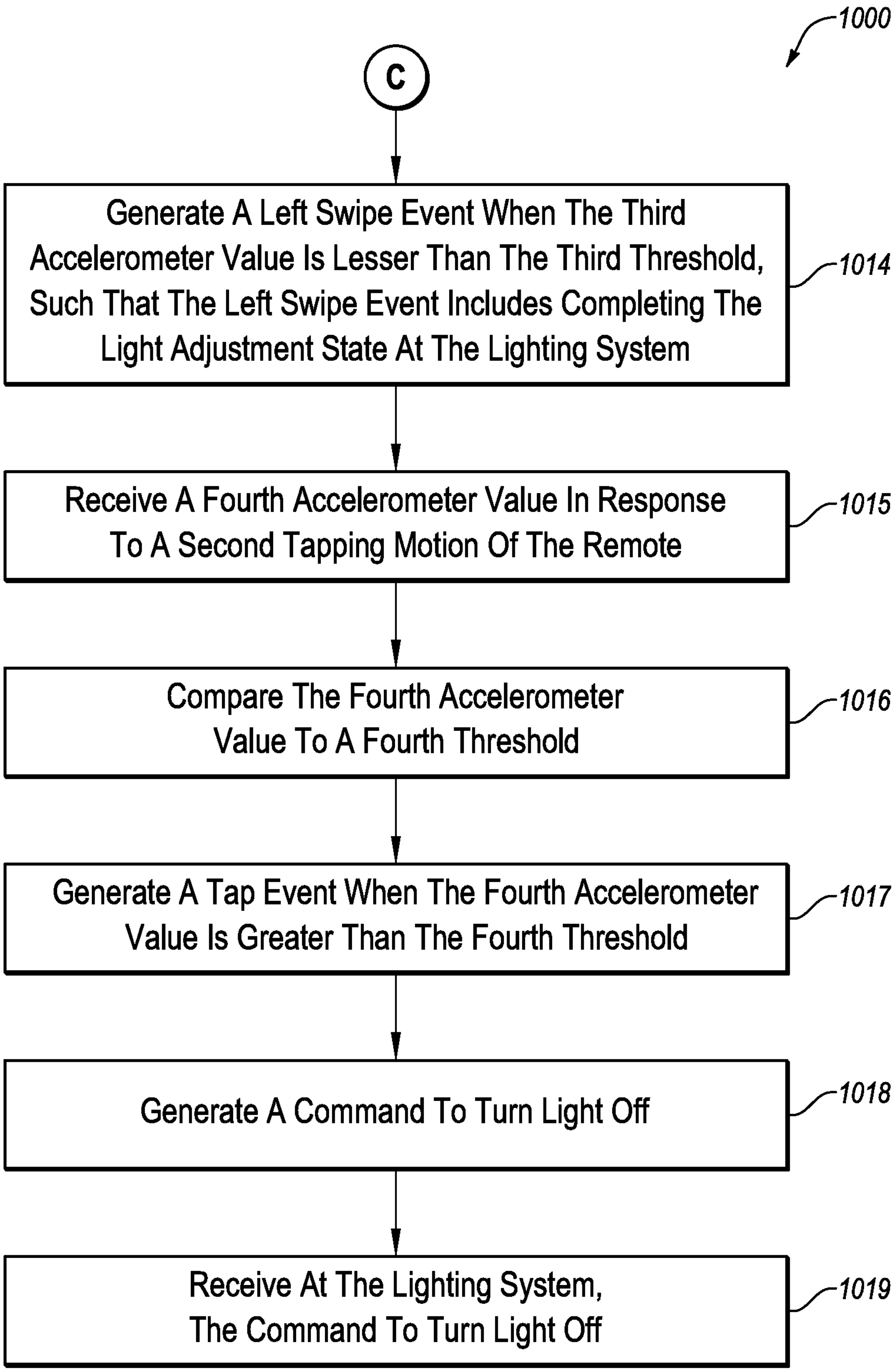

FIGS. 10A, 10B and 10C together show a flowchart of an example process 1000 which discloses working of the remote 100 as a response to a tapping motion, pointing upward motion, tilting motion, and a left swiping motion, according to some embodiments, disclosed herein. Although illustrated as discrete blocks, various blocks may be divided into additional blocks, combined into fewer blocks, or eliminated, depending on the desired implementation.

At block 1001, a first accelerometer value may be received in response to a first tapping motion of the remote 100. For example, the remote 100 may be tapped against a hard surface, such as a table, a wall, etc. In some embodiments, the acceleration sensor 106 in the remote 100 may detect the first tapping motion and generate the first accelerometer value.

At block 1002, the first accelerometer value may be compared to a first threshold value. In some embodiments, the processor 104 of the remote 100 may have the threshold value preset, and may compare the first accelerometer value to the first threshold value. In some embodiments, the tapping motion may be detected when a number of consecutive accelerometer values exceed the threshold. In other embodiments, the tapping motion may be detected when a number of consecutive accelerometer values exceed the threshold, followed by requiring one of the accelerometer values to pass a lower threshold in the opposite direction. For example, one of the accelerometer values may pass a lower threshold when the accelerometer value is lesser than a negative threshold value or when the accelerometer value is greater than a positive threshold value.

At block 1003, a tap event may be generated in the event the first accelerometer value is greater than the first threshold value.

At block 1004, the processor 104 may generate a command to turn the light on. In some embodiments, a transceiver 102 in the remote 100 may transmit a signal to a lighting system, to indicate that the light needs to be turned on.

At block 1005, the lighting system may receive the command to turn the light on. In some embodiments, a receiver unit in the lighting system may receive the signal from the transceiver 102 in the remote 100.

At block 1006, a second accelerometer value may be received in response to an upward pointing motion of the remote 100. In some embodiments, the acceleration sensor 106 in the remote 100 may detect the upward pointing motion and generate the second accelerometer value. For example, a pointing upward motion in the air may be done, using the remote 100, by the user.

At block 1007, the second accelerometer value may be compared to a second threshold value. In some embodiments, the processor 104 of the remote 100 may have the second threshold value preset, and may compare the second accelerometer value to the second threshold value. In some embodiments, a pointing upward motion may be detected when the difference between an [x,y,z] vector of accelerometer values and a vector of preset values of six axes is within a threshold value. For example, the point up motion may be detected when the absolute value of the accelerometer value along the z-axis is greater than a first threshold and the absolute values of the accelerometer values along the x-axis and y-axis are lesser than a second threshold, and the accelerometer value along the z-axis is greater than zero. In some embodiments, the six axes may include up, down, right, left, nose up, and nose down.

At block 1008, a point up event may be generated when the second accelerometer value is greater than the second threshold, such that the point event includes a light adjustment state of light at the lighting system. In some embodiments, once the remote 100 is pointed upwards or a point up event is generated, the processor 104 may enable a feature of the remote 100 such that the remote 100 may be used to adjust the light level. In some embodiments, on detecting a pointing up motion, the remote 100 may be configured to detect other different kinds of motion, such as for example, tilt motion and left swiping motion that may be used, for example, to adjust the light level.

At block 1009, a vector of accelerometer values may be received in response to a tilting motion of the remote 100. In some embodiments, the acceleration sensor 106 in the remote 100 may detect the tilting motion and generate the vector of accelerometer values. For example, a tilting motion in the air may be done, using the remote 100, by the user.

At block 1010, the extent of the tilt of the remote 100 may be determined based on the vector of acceleration values. In some embodiments, the processor 104 of the remote 100 may analyze the vector of acceleration values and compare against a threshold vector values, to generate a tilt event.

At block 1011, the intensity of the light level of the lighting system may be varied based on the extent of the tilt of the remote 100. In some embodiments, the processor 104 may determine a tilt angle or tilt value for example ‘y’ analogous to the extent of the tilt. In some embodiments, the transceiver 102 of the remote 100 may transmit a signal including the tilt value ‘y’ to a receiver unit of the lighting system so that the light level of the lighting system can be altered.

At block 1012, a third accelerometer value may be received in response to a left swiping motion of the remote 100. In some embodiments, the acceleration sensor 106 in the remote 100 may detect the left swiping motion and generate the third accelerometer value. For example, a leftward swiping motion in the air may be done, using the remote 100, by the user.

At block 1013, the third accelerometer value may be compared to a third threshold value. In some embodiments, the third threshold value may be preset in the processor 104 of the remote 100.

At block 1014, a left swipe event may be generated when the third accelerometer value is lesser than the third threshold value, such that the left swipe event includes completing the light adjustment state at the lighting system. For example, in some embodiments, the remote 100 may be configured to exit the light adjusting state at the left swiping of the remote 100. In some embodiments, the left swiping of the remote 100 may also make the light in the lighting system remain on.

At block 1015, a fourth accelerometer value may be received in response to a second tapping motion of the remote 100. For example, the remote 100 may be tapped against a hard surface, such as a table, a wall, etc. In some embodiments, the acceleration sensor 106 in the remote 100 may detect the second tapping motion and generate the fourth accelerometer value.

At block 1016, the fourth accelerometer value may be compared to a fourth threshold value. In some embodiments, the processor 104 of the remote 100 may have the threshold value preset, and may compare the fourth accelerometer value to the fourth threshold value. In some embodiments, the tapping motion may be detected when a number of consecutive accelerometer values exceed the fourth threshold. In other embodiments, the tapping motion may be detected when a number of consecutive accelerometer values exceed the fourth threshold, followed by requiring one of the accelerometer values to pass a lower threshold in the opposite direction. For example, one of the accelerometer values may pass a lower threshold when the accelerometer value is lesser than a negative threshold value or when the accelerometer value is greater than a positive threshold value.

At block 1017, a tap event may be generated in the event the fourth accelerometer value is greater than the fourth threshold value.

At block 1018, the processor 104 may generate a command to turn the light off. In some embodiments, the transceiver 102 in the remote 100 may transmit a signal to the lighting system, to indicate that the light needs to be turned off.

At block 1019, the lighting system may receive the command to turn the light off. In some embodiments, the receiver unit in the lighting system may receive the signal from the transceiver 102 in the remote 100.

Figure 11:
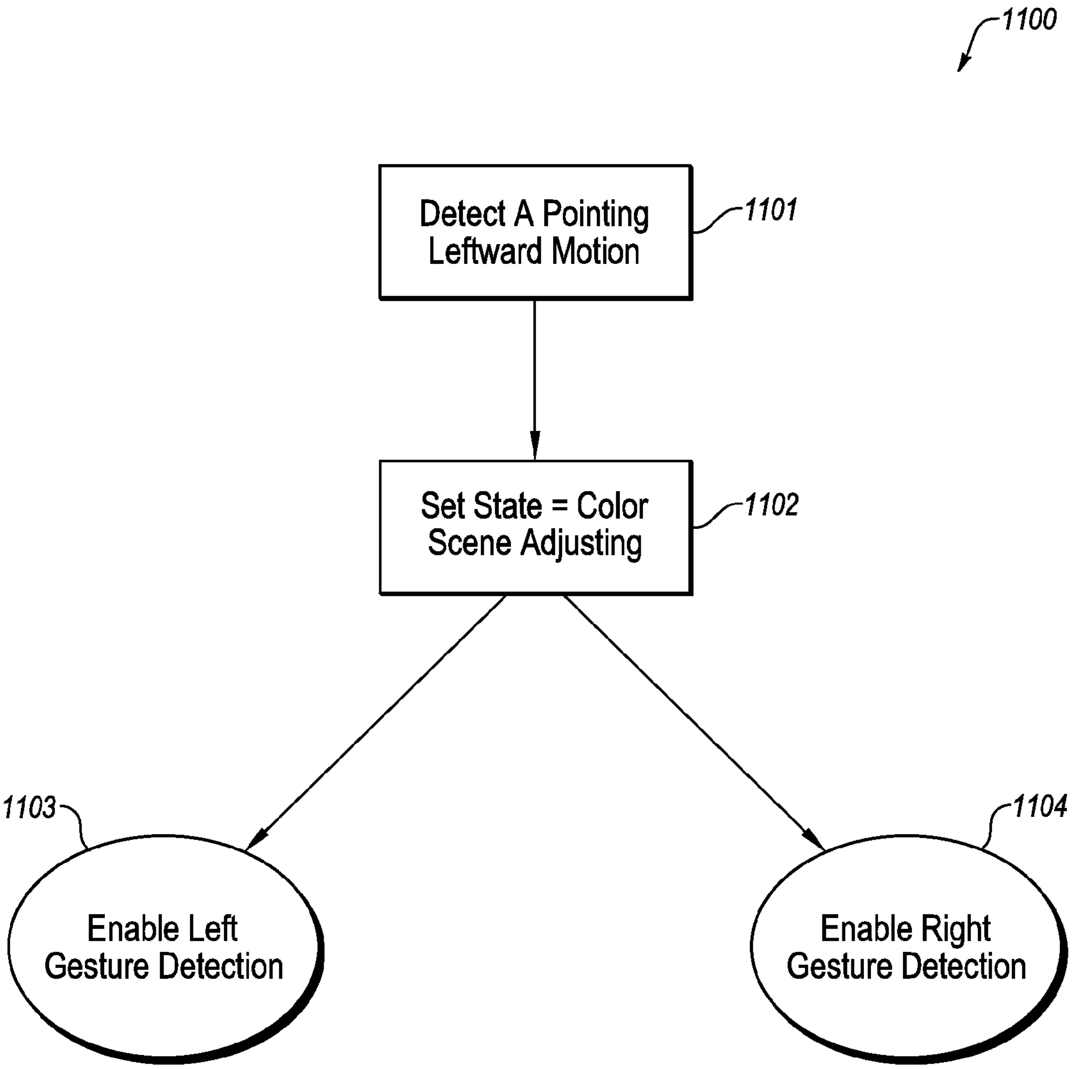
FIG. 11 shows a flowchart of an example process for color changing a lighting device according to some embodiments.

In some embodiments, such as, for example FIG. 11, color changing of light may be accomplished using the remote 100. In some embodiments, the color scene changes may be accomplished with a swipe left or swipe right motion where the swipes may change the color to a next and/or a previous color scene. In some embodiments, the enabling of the swipe left and right may be accomplished with a 90 degree roll rotation of the remote 100 to enter the state where color changes can be possible.

```
onPointLeft:
    state = colorSceneAdjusting
    enable left and right gesture detection
    set time exclusion for pointLeft(2 seconds)
onPointNormal:
        state = lightOn
onLeftGesture:
            colorSceneNumber = colorSceneNumber − 1
onRightGesture:
            colorSceneNumber = colorSceneNumber + 1
```

FIG. 11 is a flowchart of an example process 1100 showing the working of the remote 100 for color changing, in response to pointing sideways and/or a swiping motion, according to at least one embodiment. Although illustrated as discrete blocks, various blocks may be divided into additional blocks, combined into fewer blocks, or eliminated, depending on the desired implementation.

At block 1101, a point left motion is detected. Alternatively or additionally, a point right motion may be detected. For example, the point left or point right motion may be detected by the remote 100, when the difference between an [x,y,z] vector of accelerometer values and a vector of preset values of six axes is within a threshold value. For example, point left motion may be detected when the absolute value of the accelerometer value along the x-axis is greater than a first threshold value and the absolute values of the accelerometer values along the y-axis and z-axis are lesser than a second threshold value and when the accelerometer value along the x-axis is greater than zero. Upon detecting the point left motion, the process proceeds to block 1102.

At block 1102, a color scene adjusting state may be enabled. For example, the processor of the remote 100 may activate a color scene changing functionality of the remote 100, on detecting the point left motion. In some embodiments, the variable 'state', which, for example, may indicate the current state and/or setting of the light, may be set to a 'color scene adjusting' state and stored in the memory 105 of the remote 100. In some embodiments, enabling the color scene adjusting state, may enable a left gesture detection functionality and a right gesture detection functionality of the remote 100.

At block 1103, a left swipe motion of the remote 100 may be detected and the current color scene may be changed to a previous color scene. For example, after the remote 100 may detect a left swipe motion, the remote 100 may send a signal to the lighting system directing the color scheme of the light to be changed. In some embodiments, the transmitting and receiving of signals between the remote 100 and the lighting system, may occur via a transceiver 102 present in the remote 100 and a receiver unit in the lighting system. For example, the left swipe may be detected when the accelerometer value may be less than a negative threshold value. In some embodiments, the accelerometer value and the threshold value may be absolute values.

At block 1104, a right swipe motion of the remote 100 may be detected and the current color scene may be changed to a next color scene. For example, the right swipe may be detected when the accelerometer value may be greater than a positive threshold value. In some embodiments, the accelerometer value and the threshold value may be absolute values.

After either or both block 1103 or 1104, a time exclusion may be set at, for example 2 seconds, such that multiple point Left motions of the remote 100, may be excluded. In some embodiments, for example, any pointing left motion of the remote 100, after a single pointing left motion may not be acted upon for 2 seconds. In some embodiments, the time exclusion may be set at 0.5 second, 1 second, 5 seconds, 10 seconds, etc. At any point of time, if a normal pointing motion is detected, the variable 'state' will be set to the light currently being 'On' and the remote 100 will exit the color scene adjusting state. For example, on detecting a normal point motion, the processor may deactivate the color scene adjusting functionality and save the value of 'state' as 'On'. In some embodiments, a normal point motion may include pointing the remote 100 straight ahead. Although illustrated as discrete blocks, various blocks may be divided into additional blocks, combined into fewer blocks, or eliminated, depending on the desired implementation.

Figure 12:
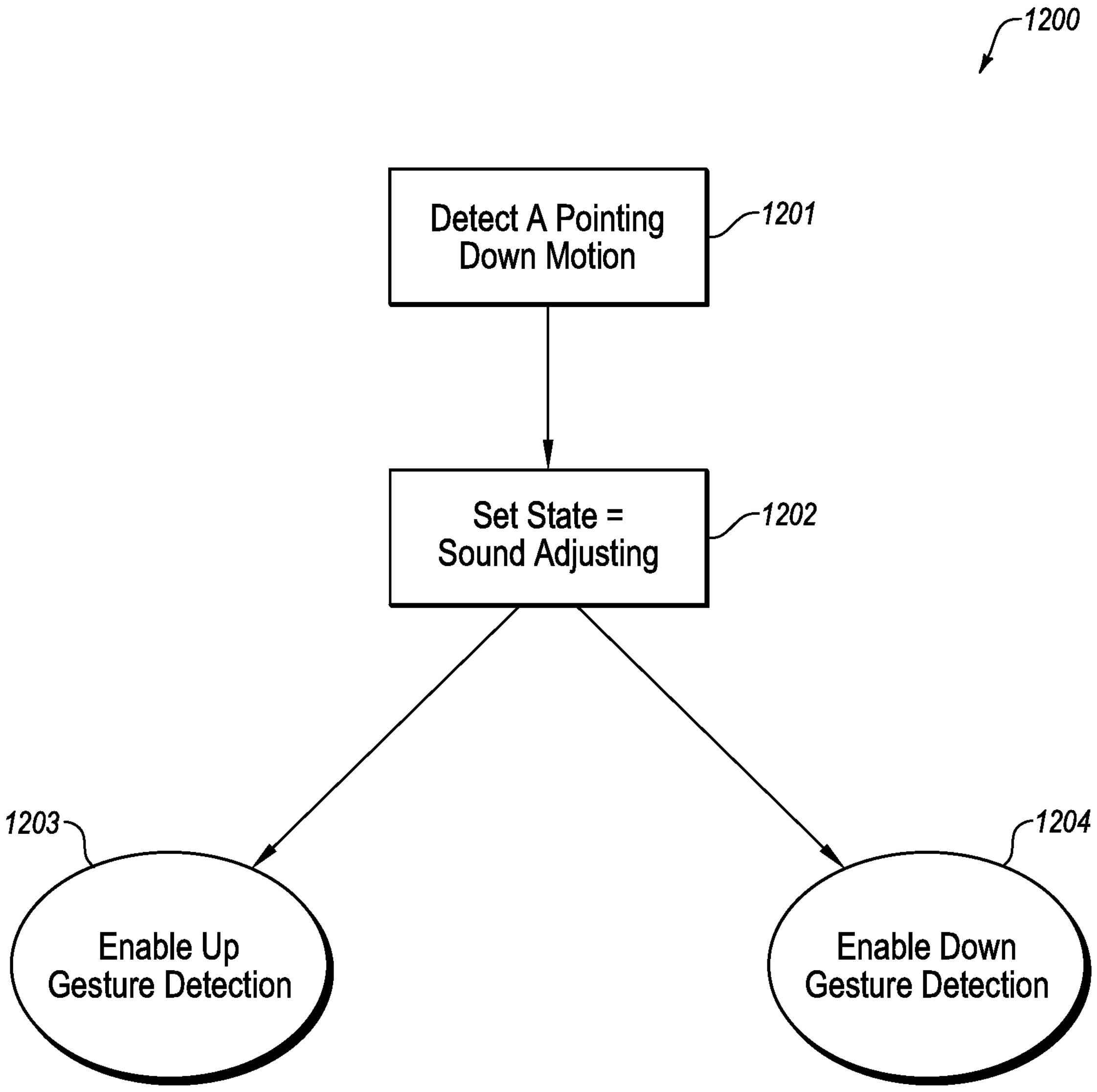
FIG. 12 is a flowchart of an example process for controlling the volume of an external device according to some embodiments.

In some embodiments, such as, for example FIG. 12, volume control of a device, for example a stereo, television, mp3 player, etc., may be accomplished using the remote 100. In some embodiments, the volume control may be accomplished with a swipe up or swipe down motion where the swipes may increase or decrease the volume.

```
onPointUpsideDown:
        state = soundAdjusting
        enable up and down gesture detection
        set time exclusion for pointUpsideDown(2 seconds)
onPointNormal:
        state = idle
onUpGesture:
      volume = volume + 1
onDownGesture:
      volume = volume − 1
```

FIG. 12 is a flowchart of an example process 1200 showing the working of the remote 100 for volume control, in response to pointing upward and pointing downward motions, according to at least one embodiment. Although illustrated as discrete blocks, various blocks may be divided into additional blocks, combined into fewer blocks, or eliminated, depending on the desired implementation.

At block 1201, a point upside down motion is detected. For example, the point upside down motion may be detected by the remote 100, when the difference between an [x,y,z] vector of accelerometer values and a vector of preset values of six axes is within a threshold value. For example, the point upside down motion may be detected when the absolute value of the accelerometer value along the z-axis is greater than a first threshold and the absolute values of the accelerometer values along the x-axis and y-axis are lesser than a second threshold, and the accelerometer value along the z-axis is lesser than zero. Upon detecting the point upside down motion, the process proceeds to block 1202.

At block 1202, a sound adjusting state may be enabled. For example, the processor 104 of the remote 100 may activate a sound changing functionality of the remote 100, on detecting the point upside down motion. The variable 'state', which for example, may indicate the current state and/or setting of the external system, may be set to a 'sound adjusting' state and stored in the memory 105 of the remote 100. In some embodiments, enabling the sound adjusting state, may enable an up gesture detection functionality and a down gesture detection functionality of the remote 100.

At block 1203, an up swipe motion of the remote 100 may be detected and the volume of an audio system may be increased. For example, the up swipe may be detected when the accelerometer value may be greater than a positive threshold value. In some embodiments, the accelerometer value and the threshold value may be absolute values.

At block 1204, a down swipe motion of the remote 100 may be detected and the volume of an audio system may be decreased. For example, the down swipe may be detected when the accelerometer value may be lesser than a negative threshold value. In some embodiments, the accelerometer value and the threshold value may be absolute values.

After either or both blocks 1203 or 1204, a time exclusion may be set at, for example 2 seconds, such that multiple point upside down motions of the remote 100, may be excluded. In some embodiments, for example, any pointing upside down motion of the remote 100, after a single pointing upside down motion, may not be acted upon during the time exclusion period. In some embodiments, the time exclusion may be set at 0.5 second, 1 second, 5 seconds, 10 seconds, etc. At any point of time, if a normal pointing motion is detected, the variable 'state' will be set to the light currently being 'On' and the remote 100 will exit the sound adjusting state. For example, on detecting a normal point motion, the processor may deactivate the sound adjusting functionality and save the value of 'state' as 'On'. In some embodiments, a normal point motion may include pointing the remote 100 straight ahead. Although illustrated as discrete blocks, various blocks may be divided into additional blocks, combined into fewer blocks, or eliminated, depending on the desired implementation.

In some embodiments, the algorithms described above may have one sensor in them including an accelerometer. In other embodiments, combinations of different sensors and user interface elements may also be used to augment the accelerometer.

In some embodiments, a traditional button or capacitive sensed touch button can be an effective augmentation to the user experience.

Process 900 and process 1000 as described above show a sequence that turns on a light, adjusts its value and then turns it back off. In some embodiments, a modified sequence using a button may also be used, which may turn the light on when the button is momentarily pressed, and then brightness may be adjusted when the button is pressed and held down, the pseudo-code for which may be as follows:

```
onButtonPress:
if ( state == lightOff)
      turn light on
      state = lightOn
      start time exclusion(500ms)
      enable point up detect
  else if (state == lightOn)
      turn light off
      state = lightOff
           start time exclusion(500ms)
onButtonHoldDown:
           state = lightAdjusting
           enable tilt
onTilt:
           set light level with tilt.y
onButtonHoldRelease:
      state = lightOn
```

In some embodiments, the addition of the button may simplify both the user experience and the algorithm to implement the same sequence.

The discussion above describes a generalized algorithm for a remote 100 for general purposes, in one of many embodiments. In some embodiments, one application of the remote 100 may be lighting control, wherein the remote 100 is a wirelessly enabled remote 100 and the lighting system may also be wirelessly enabled.

Figure 13A:
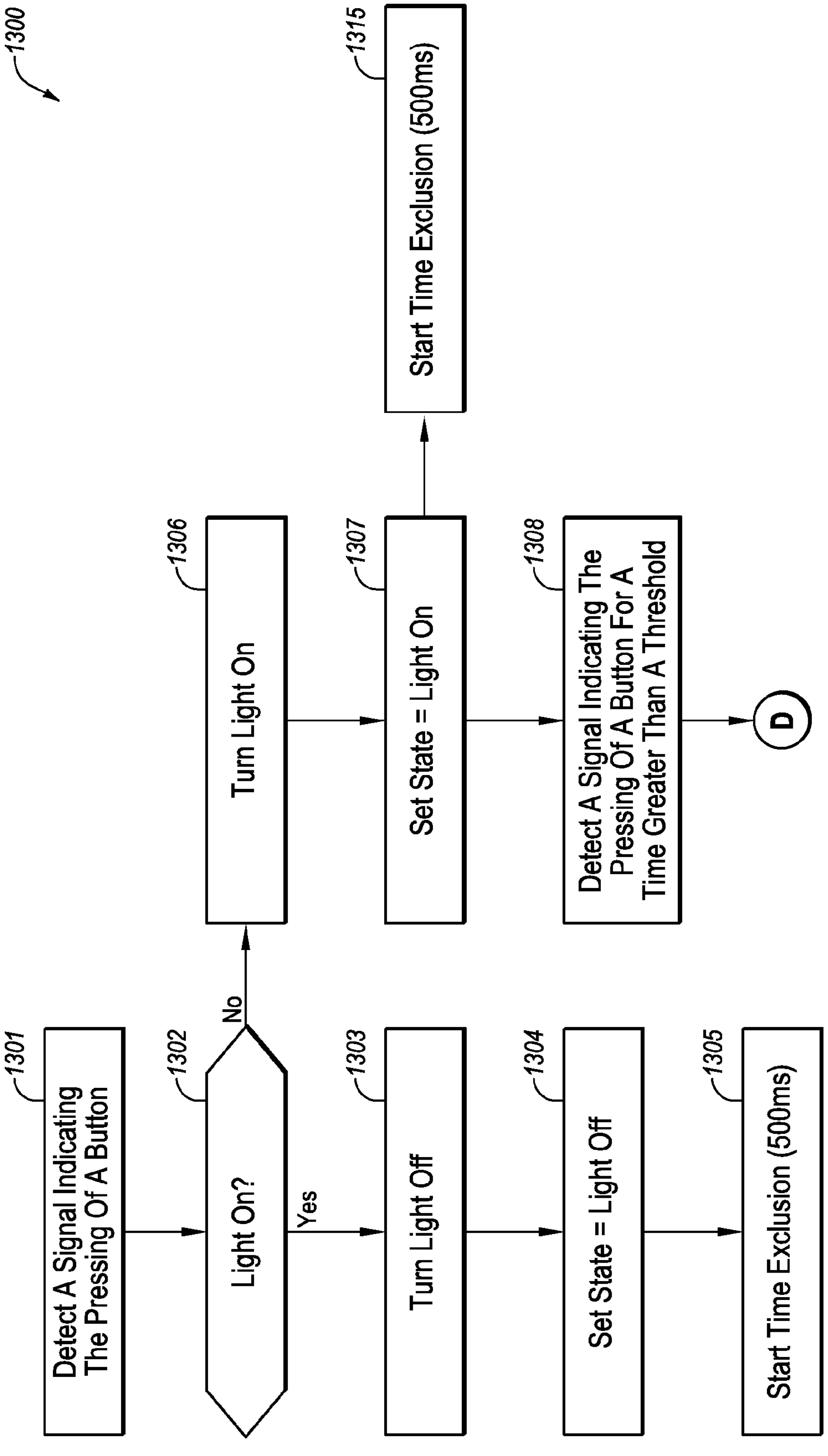
FIGS. 13A and 13B are a flowchart of an example process for controlling an external device in response to the pressing of a button according to some embodiments.
Figure 13B:
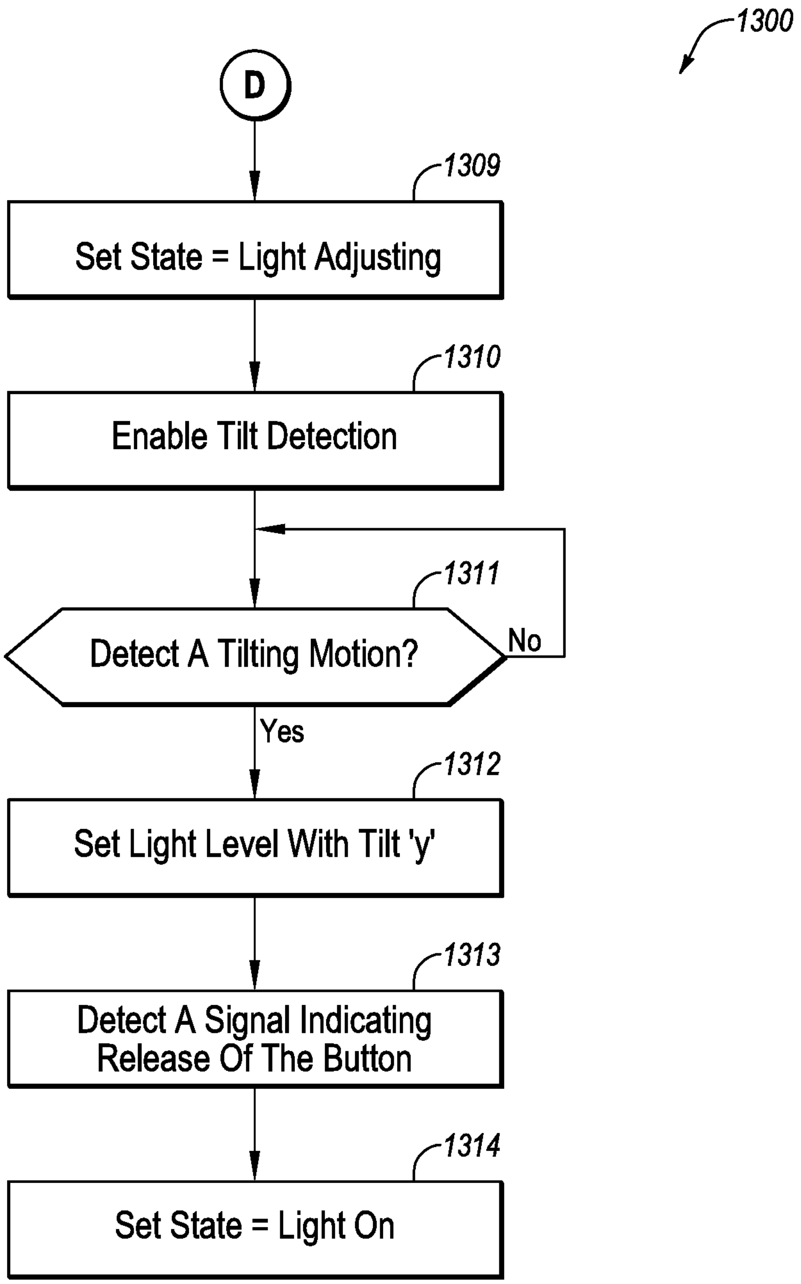

FIGS. 13A and 13B together constitute an example flowchart of a process 1300 that discloses the working of the remote 100 as a response to the pressing of a button. Although illustrated as discrete blocks, various blocks may be divided into additional blocks, combined into fewer blocks, or eliminated, depending on the desired implementation.

At block 1301, a signal may be detected to indicate the pressing of the button. In some embodiments, the processor 104 of the remote 100 may receive a first minor electrical surge signal to detect the pressing of the button.

At block 1302, upon the button having been pressed, it may be checked whether the current state of light in a lighting system is on or off. In some embodiments, in the event the light is on, the light is turned off as shown in block 1303. At block 1304, the processor 104 may set a state to 'lightOff'.

At block 1305, a time exclusion may be set such as, for example, at 500 ms, such that multiple pressing of the button of the remote 100, may be excluded from causing the remote 100 to change the state of the light. The time exclusion may also be at 250 ms, 750 ms, 1,000 ms, 1,500 ms, etc. In some embodiments, for example, any pressing of the button of the remote 100, after a single pressing of the button may not be acted upon until the time exclusion period has been reached. For example, the processor 104 within the remote 100, may detect the multiple pressing of the button of the remote 100, but may not send any signal or information to the lighting system to turn the light 'Off', based on any pressing of the button of the remote 100 that may occur during the time exclusion period after the first pressing of the button of the remote 100.

At block 1302, if it is detected that the current state of light in the lighting system is off, the light may be turned on at block 1306, and the processor 104 of the remote 100 may set the state of the light as 'lightOn' at block 1307.

At block 1308, the processor 104 of the remote 100 may detect a signal indicating the button of the remote 100 being pressed and held for a time greater than a threshold time, after the state of the light in the lighting system has been set to 'lightOn'. In some embodiments, the threshold time may be preset in the processing system of the remote 100.

At block 1309, the state may be reset into a 'light adjusting' state. In some embodiments, the state may be set to the 'light adjusting' state in the event the signal indicating the button of the remote 100 being pressed and held for a time greater than a threshold time has been received. In some embodiments, as a result of the 'light adjusting' state being enabled, a tilt motion detection may be enabled, as shown in block 1310.

At block 1311, the remote 100 may be enabled to detect any tilting motion of the remote 100. In some embodiments, in the event a tilting motion is detected, a tilt angle 'y' may then be determined.

At block 1312, in some embodiments, upon the tilt motion being detected, for example, once the remote 100 is tilted, the processor 104 may enable a feature of the remote 100 such that the light intensity level may be altered or varied based on the tilt angle 'y'. In some embodiments, the more the tilt is in a first direction, the more the light may be dimmed. In some embodiments, the more the tilt is n a second direction, the lesser the light may be dimmed. In some embodiments, the second direction may include a direction opposite to the first direction.

At block 1313, the processor 104 of the remote 100 may receive a signal indicating release of the button that was being pressed. In some embodiments, the processor 104 may detect a second minor surge of an electrical signal to detect the release of the button being pressed. In some embodiments, the second minor surge of the electrical signal may be in an opposite direction compared to the first minor surge of the electrical signal.

At block 1314, the processor 104 may set the state of the lights in the lighting system as 'lightOn', indicating the current state of the light at the lighting system to be 'On' and also may deactivate the light adjusting state of the remote 100.

At block 1315, a time exclusion may be set such as, for example, at 500 ms, such that multiple pressing of the button of the remote 100, may be excluded from causing the remote 100 to change the state of the light. The time exclusion may also be at 250 ms, 750 ms, 1,000 ms, 1,500 ms, etc. In some embodiments, for example, any pressing of the button of the remote 100, after a single pressing of the button may not be acted upon until the time exclusion period has been reached. For example, the processor 104 within the remote 100, may detect the multiple pressing of the button of the remote 100, but may not send any signal or information to the lighting system to turn the light 'On', based on any pressing of the button of the remote 100 that may occur during the time exclusion period after the first pressing of the button of the remote 100.

In some embodiments, a pressing of the button of the remote 100, following the deactivation of the light adjusting state of the remote 100, may be detected as described in block 1301 followed by 1302, and the light may then be turned 'Off'. Although illustrated as discrete blocks, various blocks may be divided into additional blocks, combined into fewer blocks, or eliminated, depending on the desired implementation.

While the examples stated above show a few possibilities of how the remote 100 can be applied to lighting control, other scenarios are also possible. In some embodiments, control of light intensity, color, direction, initial configuration and commissioning and other lighting parameters may be controlled with a combination of accelerometer, button and other sensor events.

In some embodiments, for an accelerometer enabled remote 100, the power usage of the hardware and software in the remote 100 can be critical. The above described event recognition system could possibly consume significant power by having a CPU analyze each and every accelerometer sample at 200 Hz or faster. Thus, in some embodiments, the remote 100 may be so designed as to be able to charge the remote 100 while holding the remote 100 against the wall.

In some embodiments, the remote 100 may be capable of detecting a grip over a touch. In some embodiments, the remote 100 may include a capacitive touch pad that may detect a gripping of the remote 100 or the remote 100 being held by the user. In some embodiments, the gripping of the remote 100 may lead to the turning on of the remote 100. In some embodiments, an accelerometer value when greater than a set threshold, may lead to the turning on of the remote 100. In some embodiments, this feature may help increase the battery life of the remote 100. In some embodiments, the grip detection may help distinguish between a scenario where the remote 100 may be mistakenly tapped on by a touch of the hand, and the scenario where the remote 100 may be gripped by the hand. In some embodiments, the remote 100 may be in a grip detection mode, when the battery level is less than a threshold value. In some embodiments, a starting signal may be generated upon detection of the remote 100 being held by the user or being gripped by the user, such that the starting signal may indicate that the remote 100 has been switched on.

There are various strategies for enabling long battery life, however. In some embodiments, only the events of interest may be enabled so that the CPU can stay in a low power mode and not be bothered for processing events that may not be of current interest. In some embodiments, the exclusions layer 203 may be a part of achieving low power, as the exclusions layer 203 may determine the events to be passed on to the action layer 204 and the events to be excluded.

In some embodiments, transferring a part of the processing to the accelerometer itself may be a second method of enabling low power operation. In some embodiments, an ST Electronics LIS2DH12 accelerometer may be used, as this chip has a threshold detection, high pass filtering, selectable sample rate and resolution and other features, that may enable some of the functionalities of the event recognition layer 202 in the accelerometer, and then the CPU may be configured to perform only the higher level events. In some embodiments, other accelerometers may be used.

Figure 14:
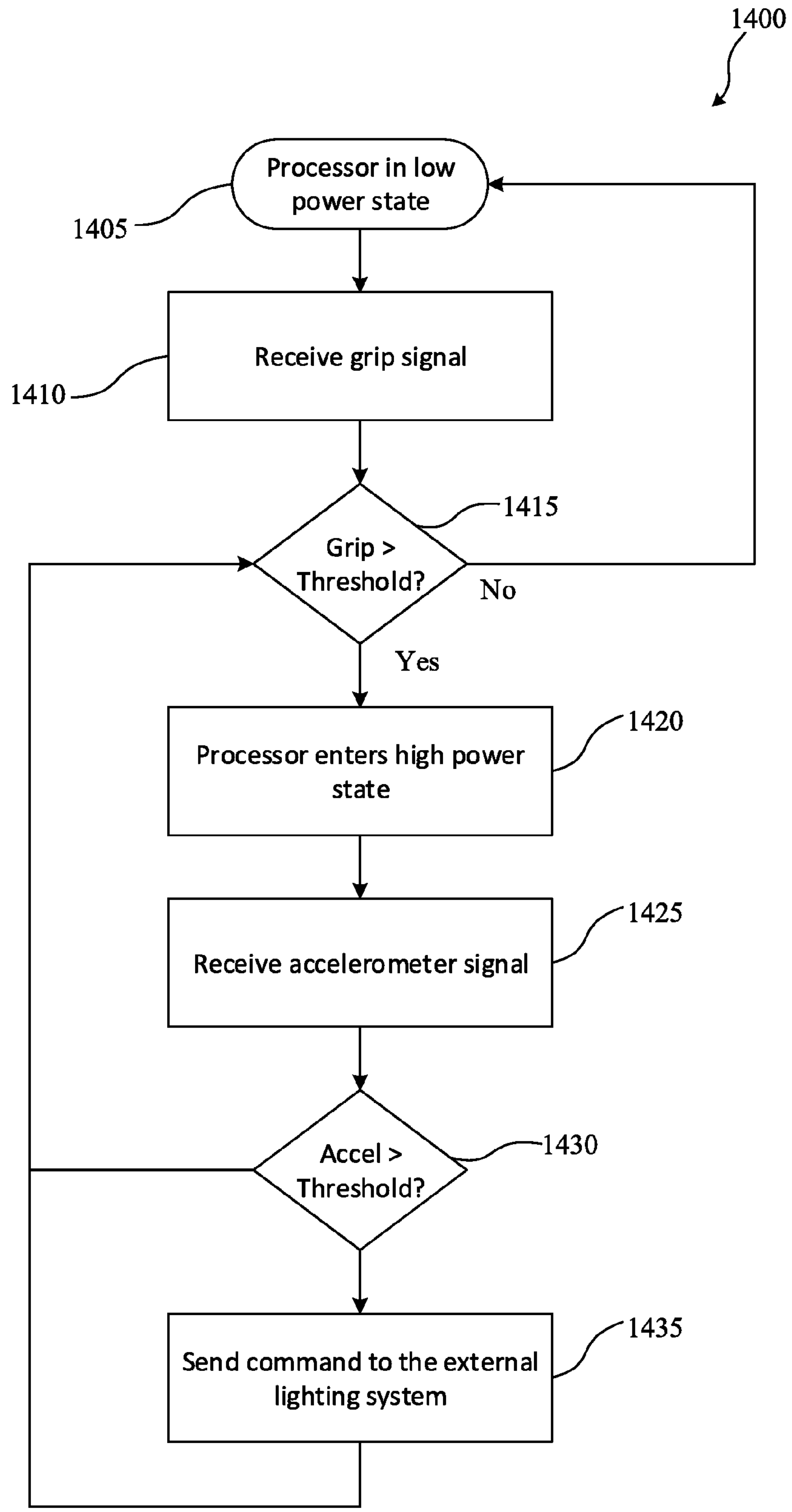
FIG. 14 is a flowchart of an example process for a remote according to some embodiments.

FIG. 14 is a flowchart of an example process 1400 for a remote according to some embodiments. Process 1400 begins at block 1405 where the processor 104 of the remote 100 is in a low power state. In a low power state, the processor 104 may perform a limited subset of functions and/or consumer less power than when the processor 104 is in a high power state. In some embodiments, the processor 104 may receive and analyze grip signals during the low power state. In some embodiments, in the low power state the processor 104 may not analyze acceleration signals such as, for example, from an accelerometer.

At block 1410 a grip signal may be received from a user interface such as, for example, a touch pad or a capacitive touch pad. The grip signal, for example, may have a digital value representing the pressure on the grip sensor or the amount of grip, the surface area gripped, the time period of a grip, a combination thereof, etc. In some embodiments, the grip signal may be filtered, digitized, etc.

At block 1415 it can be determined whether the grip signal represents a grip event from a user. This may be determined, for example, by calculating whether the grip value of a sensor signal is greater than a threshold. If the sensor signal is less than a predetermined threshold amount, then process 1400 returns to block 1405. If the grip signal is greater than a predetermined threshold amount, then process 1400 proceeds to block 1420. Alternatively or additionally, a grip event can be identified by mathematically determining whether the sensor signal is consistent with a user-initiated event such as, for example, by averaging, integrating, filtering, etc. a sensor signal over time.

At block 1420 the processor enters a high power state. At a minimum, in a high power state accelerometer signals are received and/or analyzed, whereas in a low power state accelerometer signals are not received and/or analyzed.

At block 1425 an accelerometer signal may be received. In some embodiments, the accelerometer signal may be filtered, digitized, etc.

At block 1430 it can be determined whether the accelerometer signal is greater than a threshold value. If the accelerometer signal is less than a predetermined threshold amount, then process 1400 returns to block 1415. If the accelerometer signal is greater than a predetermined threshold amount, then process 1400 proceeds to block 1435. Alternatively or additionally, an acceleration event can be identified by mathematically determining whether the acceleration signal is consistent with a user-initiated event such as, for example, by averaging, integrating, filtering, etc. an acceleration signal over time.

At block 1435 a command may be sent to an external device in response to the accelerometer signal being greater than the threshold value. In some embodiments, the command may include a value that is proportional to at least a portion of the accelerometer signal. For example, any signal disclosed in this document or not maybe sent to the external device. After block 1435, process 1400 returns to block 1415.

While, the above discussion has focused on the application of the accelerometer user interface and user experience to a remote 100, in some embodiments, the same system can be applied to a Mobile Application running on a smart phone such as an iPhone, Apple Watch, Android or other smart devices. In some embodiments, these smart phones may contain accelerometers and the Mobile applications on these phones can be configured to access the accelerometers. In some embodiments, the Mobile Applications may use the same system described above to achieve advanced user interfaces and experiences for lighting and other applications. While the above system describes physical tactile or capacitive buttons, in some embodiments, a mobile application may use on-screen user interface elements in place of the physical tactile or capacitive buttons. For example, in the press-and-hold example of changing a dimming level for a lighting system, a physical button press above may be replaced with an on-screen button press in the mobile application. In other embodiments, the initial orientation of the remote 100 may be used to select which target device is to be controlled. For example if the default orientation is used, the remote 100 could be used to control the lights; if the remote 100 is rotated by 90 degrees, the remote 100 may then be used to change the stereo whereas a 180 degree rotation could be used to select the front door lock.

Numerous specific details are set forth to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

That which is claimed:

1. A remote for gesture recognition m an external lighting system comprising:

an acceleration sensor; a wireless transceiver; memory; and a processor communicatively coupled with the acceleration sensor, the wireless transceiver, and the memory, the processor configured to:

sample first acceleration data and second acceleration data from the acceleration sensor;

determine a first event type based on the first acceleration data, wherein the first event type comprises one or more events selected from the list consisting of a swipe, a tap, a double tap, a directional point, and a tilt;

determine a second event type based on the second acceleration data, wherein the second event type comprises one or more events selected from the list consisting of a swipe, a tap, a double tap, a directional point, and a tilt;

exclude the second event type;

determine a command for an external lighting system based on the first event type; and transmit the command to the external lighting system using the wireless transceiver.

2. The remote according to claim 1, wherein the acceleration data comprises a vector of accelerometer values along an x-axis, y-axis, and z-axis.

3. The remote according to claim 1, wherein excluding the second event occurs when it is determined that the second event is similar to the first event but time lagged.

4. The remote according to claim 1, wherein the first event comprises an acceleration along a first axis and the second event comprises an acceleration along one or more axes orthogonal to the first axis.

5. The remote according to claim 1, wherein determining a first event type based on the acceleration data further comprises determining whether at least a portion of the acceleration data is greater than a first threshold value, and wherein determining a second event type based on the acceleration data further comprises determining whether the at least a portion of the acceleration data is greater than a second threshold value.

6. The remote according to claim 1, further comprising a touch sensor, and wherein the processor may be further configured to:

receive grip data from the touch sensor indicating that a user has gripped the remote prior to transmitting the command to the external device; and determine whether the grip data is greater than threshold, wherein the command is transmitted to the external device using the wireless transceiver in the event the grip data is greater than the threshold.

7. The remote according to claim 1, wherein the first event type comprises a tilt of the remote, and the command comprises a command to dim lights a given dim amount at the external lighting system.

8. The remote according to claim 7, wherein the given dim amount corresponds with the first acceleration data.

9. The remote according to claim 1, wherein the first event type comprises a swipe; and wherein the command for an external lighting system comprises a command to change the color an amount proportional to the swipe.

10. A method comprising:

receiving an acceleration signal generated by an acceleration sensor m response to a physical motion of a remote;

filtering the acceleration signal from the acceleration sensor;

mathematically determining whether the acceleration signal is consistent with a user-initiated event;

determining an action to be taken at an external lighting system, based on the determination that the acceleration signal is consistent with the user-initiated event; and sending a command to the external lighting system based on the action determined.

11. The method of claim 10, wherein mathematically determining whether the acceleration signal is consistent with a user-initiated event includes comparing an acceleration value derived from the acceleration signal with a threshold value.

12. The method of claim 10, wherein the acceleration value corresponds with a tap, and the action to be taken comprises changing a state of the external lighting system.

13. The method of claim 10, wherein the acceleration value corresponds with a tilt, and the action to be taken comprises setting a dimming level of the external lighting system.

14. The method of claim 10, wherein the physical motion comprises gripping, tapping, conductor tapping, swiping, tilting, and/or pointing.

15. The method of claim 10, wherein mathematically determining whether the acceleration value is consistent with a user-initiated event includes determining acceleration along one axis in one direction and/or along multiple axes in multiple directions.

16. The method of claim 10, further comprising:

receiving grip data from a touch sensor indicating that a user has gripped the remote prior to transmitting the command to the external device; and determining whether the grip data is greater than a threshold, wherein the command is transmitted to the external device using a wireless transceiver in the event the grip data is greater than the threshold.

17. The method of claim 16, further comprising:

receiving grip data from a touch sensor indicating that a user has gripped the remote prior to transmitting the command to the external device; and entering a high power state.

18. A remote for gesture recognition m an external lighting system comprising:

a user interface sensor;

a wireless transceiver;

memory; and a processor communicatively coupled with the user interface sensor, the wireless transceiver, and the memory, the processor configured to:

sample first sensor data and second sensor data from the user interface sensor;

filter the first sensor data and second sensor data from the interface sensor;

determine a first event type based on the first sensor data, wherein the first event type comprises one or more events selected from the list consisting of a swipe, a tap, a double tap, a directional point, a press and hold, a press, a hold, and a tilt;

determine a second event type based on the second sensor data, wherein the second event type comprises one or more events selected from the list consisting of a swipe, a tap, a double tap, a directional point, a press and hold, a press, a hold, conductor's tap, and a tilt;

determine a command for an external lighting system based on the first event type and the second event type; and transmit the command to the external lighting system using the wireless transceiver.

19. The remote according to claim 18, wherein first event type includes grip event and the second event type includes a tilt event.

20. The remote according to claim 18, wherein first event type includes grip event and the second event type includes a tap event.

21. The remote according to claim 18, wherein first event type includes grip event and the second event type includes a directional point event.

22. The remote according to claim 18, wherein first event type includes button press and hold event and the second event type includes a tilt event.

23. The remote according to claim 18, wherein first event type includes button press event and the second event type includes a tap event.

24. The remote according to claim 18, wherein first event type includes button press event and the second event type includes a directional point event.

25. The remote according to claim 18, wherein determining a command for an external lighting system based on the first event type and the second event type includes determining the second event type should be excluded.

26. The remote according to claim 18, wherein the user interface sensor comprises either or both an accelerometer and a touch sensor.

27. The remote according to claim 18, further comprising an accelerometer coupled with the processor;

wherein the user interface sensor comprises a capacitive touch sensor; wherein the first event type comprises either or both a tilt event from the accelerometer and/or a press and hold event on the user interface sensor; and wherein the command for an external lighting system comprises a command to change the color an amount proportional to the tilt.

* * * * *